(12) United States Patent
Unutmaz et al.

(10) Patent No.: US 8,703,128 B2
(45) Date of Patent: Apr. 22, 2014

(54) METHODS OF MODULATING TGFβ SIGNALING

(75) Inventors: Derya Unutmaz, New York, NY (US); Aimee El Hed, Morrisville, NC (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/355,798

(22) Filed: Jan. 23, 2012

(65) Prior Publication Data

US 2012/0251523 A1 Oct. 4, 2012

Related U.S. Application Data

(60) Provisional application No. 61/461,857, filed on Jan. 24, 2011.

(51) Int. Cl.
| | | |
|---|---|---|
| A61K 39/395 | (2006.01) | |
| C12N 15/11 | (2006.01) | |
| A61K 38/46 | (2006.01) | |
| G01N 33/573 | (2006.01) | |

(52) U.S. Cl.
USPC .................. 424/130.1; 514/44 A; 424/94.67; 435/7.4

(58) Field of Classification Search
None
See application file for complete search history.

(56) References Cited

FOREIGN PATENT DOCUMENTS

| WO | 2005/111626 | 11/2005 |
|----|-------------|---------|
| WO | 2006/014903 | 2/2006 |

OTHER PUBLICATIONS

Le Pabic et al. Involvement of the serine/threonine p70s6 kinase in TGF-beta1-induced ADAM12 expression in cultured human hepatic stellate cells. Journal of Hepatology. 43(6):1038-1044, 2005.*
Oh et al. Structure based virtual screening and biological evaluation of potent and selctive ADAM12 inhibitors. Bioorganic and Medicinal Chemistry Letters. 14:6071-6074, 2004.*
Fridman et al. Selective Inhibition of ADAM Metalloproteases as a Novel Aproach for Modulating ErbB Pathways in Cancer. Clinical Cancer Research.13(6):1892-1902, 2007.*
Atfi et al. The disintegrin and metalloproteinase ADAM12 contributes to TGF-beta signaling through interaction with the type II receptor. Journal of Cell Biology. 178(2): 201-208, 2007.*
Okada et al. ADAM-12 (Meltrin alpha) is involved in chondrocyte proliferation via cleavage of insulin-like growth factor binding protein 5 in osteoarthritic cartilage. Arthritis and Rheumatism, 58(3):778-789, Mar. 2008.*
Reiss, et al. "The "A disintegrin and metalloprotease" (ADAM) family of sheddases: physiological and cellular functions", Semin Cell Dev Biol (2009) 20, 126-137.
White, "ADAMS: Modulators of cell-cell and cell-matrix interactions", Curr Opin Cell Biol (2003) 15, 598-606.
Gilpin, et al. "A novel secreted form of human ADAM12 (meltrin alpha) provokes myogenesis in vivo", J Biol Chem (1998) 273, 157-166.
Cao, et al. "Intracellular processing of metalloprotease disintegrin ADAM12", J Biol Chem (2002) 277, 26403-26411.
Loechel, et al. "Human ADAM12 (meltrin alpha) is an active metalloprotease", J Biol Chem (1998) 273, 16993-16997.
Yagami-Hiromasa, et al. "A metalloprotease-disintegrin participating in myoblast fusion", Nature (1995) 377, 652-656.
Kawaguchi, et al. "ADAM12 protease induces adipogenesis intransgenic mice", Am J Pathol (2002) 160, 1895-1903.
Harold, et al. "Interaction between the ADAM12 and SH3MD1 genes may confer susceptibility to late-onset Alzheimer's disease", Am J Med Genet B Neuropsychiatr Genet (2007) 144B, 448-452.
Spencer, et al. "ADAM12 as a marker of trisomy 18 in the first and second trimester of pregnancy", J Matern Fetal Neonatal Med (2007) 20, 645-650.
Torring, et al. "First trimester screening for trisomy 21 in gestational week 8-10 by ADAM12-S as a maternal seunn marker", Reprod Biol Endocrinol 8, 129, Publication date—Oct. 29, 2010.
Wang, et al. "Matrix metalloproteinase-7 and ADAM-12 (a disintegrin and metalloproteinase-12) define a signaling axis in agonist-induced hypertension and cardiac hypertrophy", Circulation (2009) 119, 2480-2489.
Kveiborg, et al. "Cellular roles of ADAM12 in health and disease", Int J Biochem Cell Biol (2008) 40, 1685-1702.
Toft-Hansen, et al. "Key metalloproteinases are expressed by specific cell types in experimental autoimmune encephalomyelitis", J Immunol (2004) 173, 5209-5218.
Atfi, et al. "The disintegrin and metalloproteinase ADAM12 contributes to TGF-beta signaling thorugh interaction with the type II receptor", J Cell Biol (2007) 178, 201-208.
Solomon, et al. "The role of SnoN in transforming growth factor beta1-induced expression of metalloprotase-disintegrin ADAM12", J Biol Chem 285, 21969-21977, publication date—Jul. 16, 2010.
Todorovic, et al. "Latent TGF-beta binding proteins", Int J Biochem Cell Biol (2005) 37, 38-41.
Taylor, "Review of the activation of TGF-beta in immunity", J Leukoc Biol (2009) 85, 29-33.

(Continued)

Primary Examiner — Vanessa L Ford
Assistant Examiner — Sandra Dillahunt
(74) Attorney, Agent, or Firm — Klauber & Jackson LLC

(57) ABSTRACT

The present invention provides methods of identifying the presence of or quantifying the amount of one or more of T helper (Th) cells and iTreg cells present in a sample by identifying the presence of an ADAM or the amount of an ADAM, such as ADAM12, present in a sample. The present invention also provides methods for increasing or decreasing signaling of a TGF such as TGFβ by increasing or decreasing the biological activity or expression of an ADAM. Further, the present invention provides methods for inhibiting or stimulating, downregulating or upregulating, an immune response, and for treating diseases associated with an immune response such as cancer, viral, bacterial and fungal infections, autoimmune diseases and graft versus host diseases. Still further, the invention provides screening methods effective for identifying therapeutic agents, pharmaceutical compositions containing therapeutic agents, and vaccines.

6 Claims, 13 Drawing Sheets

(56) References Cited

OTHER PUBLICATIONS

Wipff, et al. "Integrins and the activation of latent transforming growth factor beta1—an intimate relationship", Eur J Cell Biol (2008) 87, 601-615.

Glinka, et al. "Neuropilin-1 is a receptor for transforming growth factor beta-1, activates its latent form, and promotes regulatory T cell activity", J Leukoc Biol (2008) 84, 302-310.

Chen, et al. "Latency-associated peptide identifies a novel CD4+CD25+ regulatory T cell subset with TGF beta-mediated function and enhanced suppression of experimental autoimmune encephalomyelitis", J Immunol (2008) 180, 7327-7337.

Massague, "A very private TGF-beta receptor embrace", Mol Cell (2008) 29, 149-150.

Blobe, et al. "Role of transforming growth factor beta in human disease", N Engl J Med (2000) 342, 1350-1358.

Li, et al. "TGF-beta: a master of all T cell trades", Cell (2008) 134, 392-404.

Bettelli, et al. "Reciprocal developmental pathways for the generation of pathogenic effector TH17 and regulatory T cells", Nature (2006) 441, 235-238.

Mangan, et al. "Transforming growth factor-beta induces development of the T(H)17 lineage", Nature (2006) 441, 231-234.

Travis, et al. "Loss of integrin alpha(V)beta 8 on dendritic cells causes autoimmunity and colitis in mice", Nature (2007) 449, 361-365.

Gruel et al., "In silico investigation of ADAM12 effect on TGF-beta receptors trafficking", BMC Research Notes (2009); 2:193.

* cited by examiner

FIG. 1A
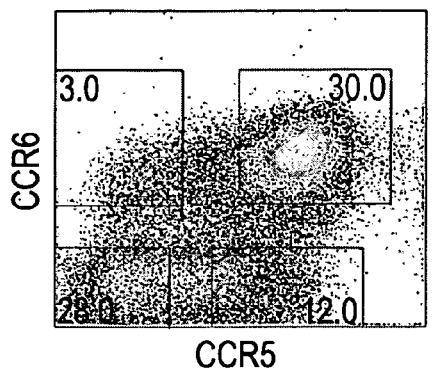
FIG. 1B
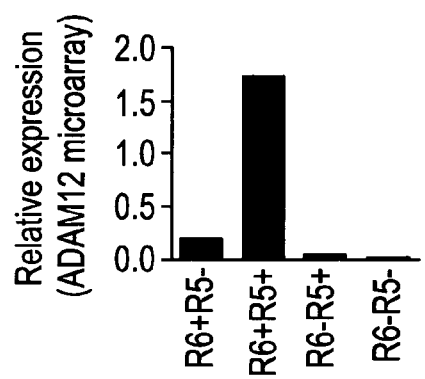
FIG. 1C
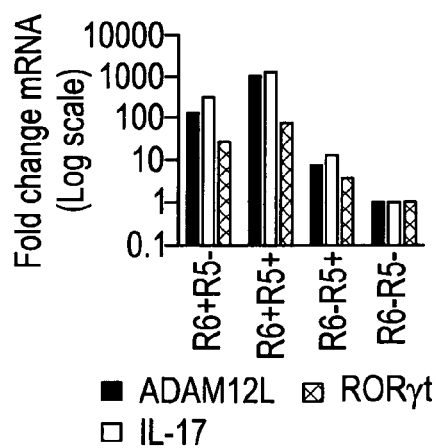
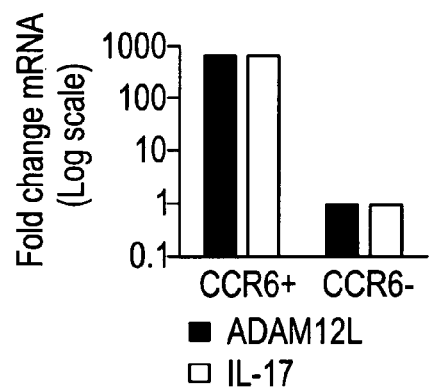
FIG. 1D
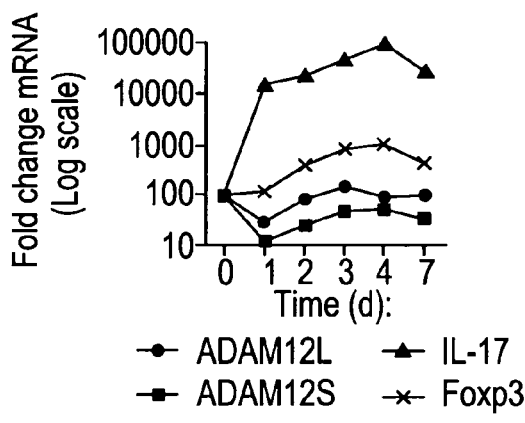
FIG. 1E
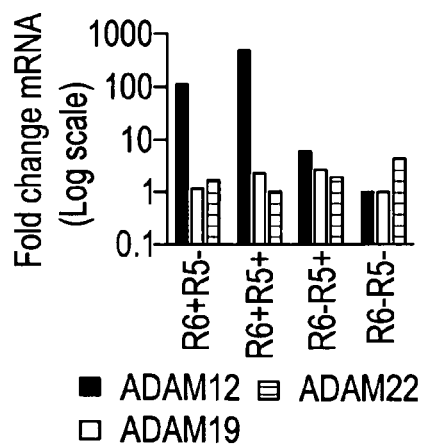

FIG. 2C
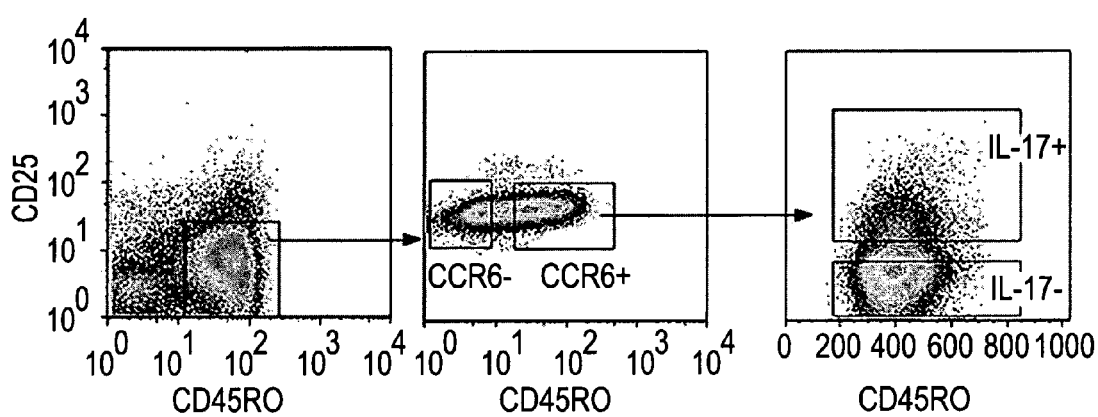
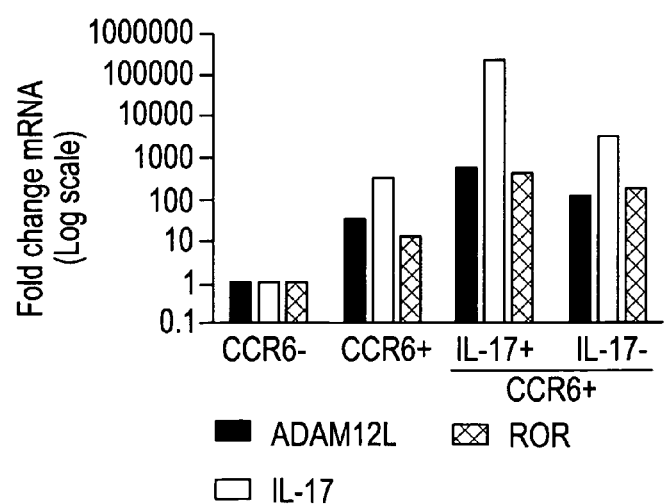

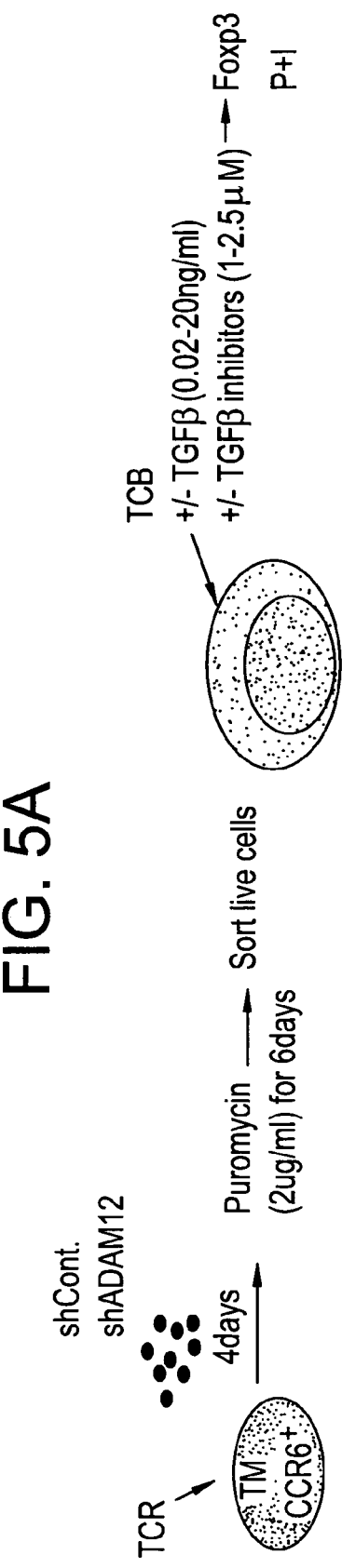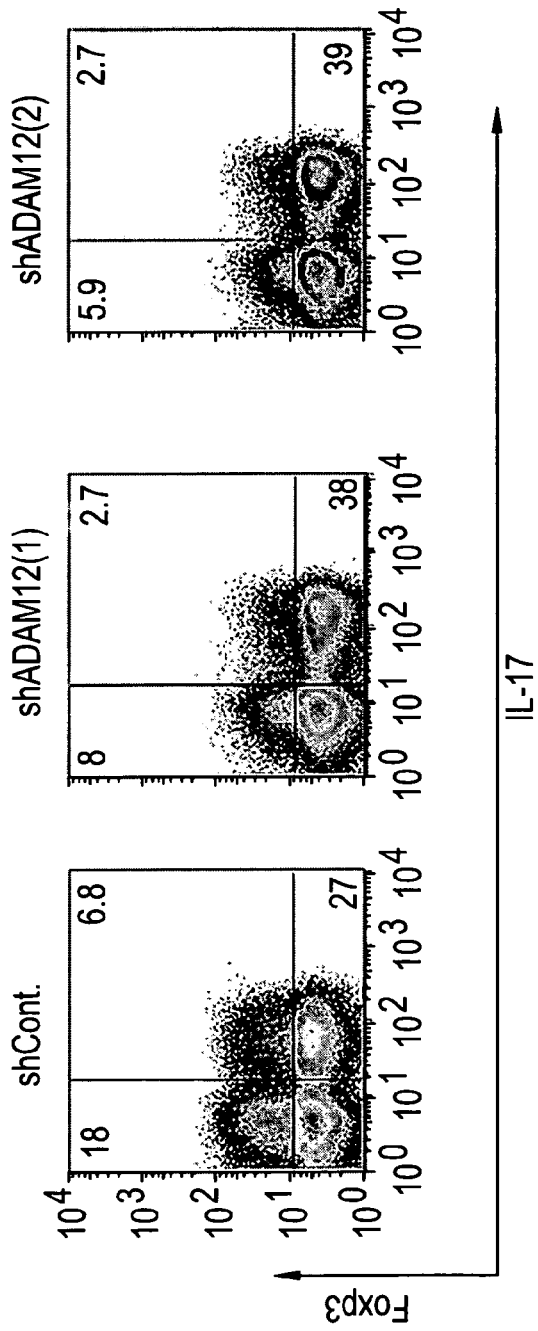
FIG. 5A
FIG. 5B

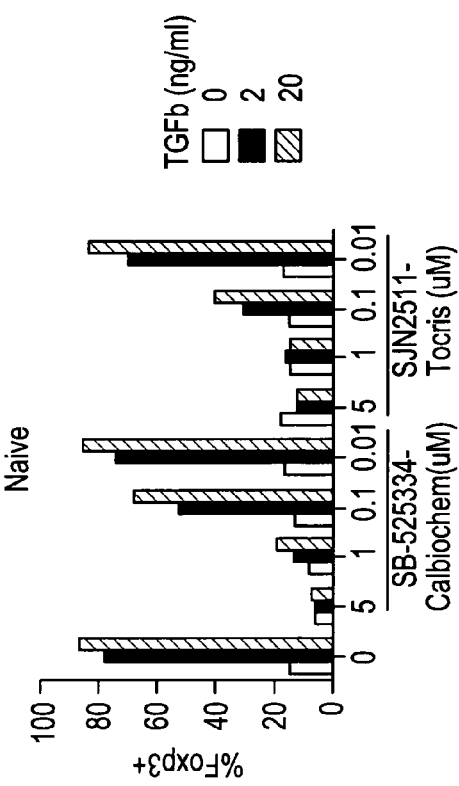
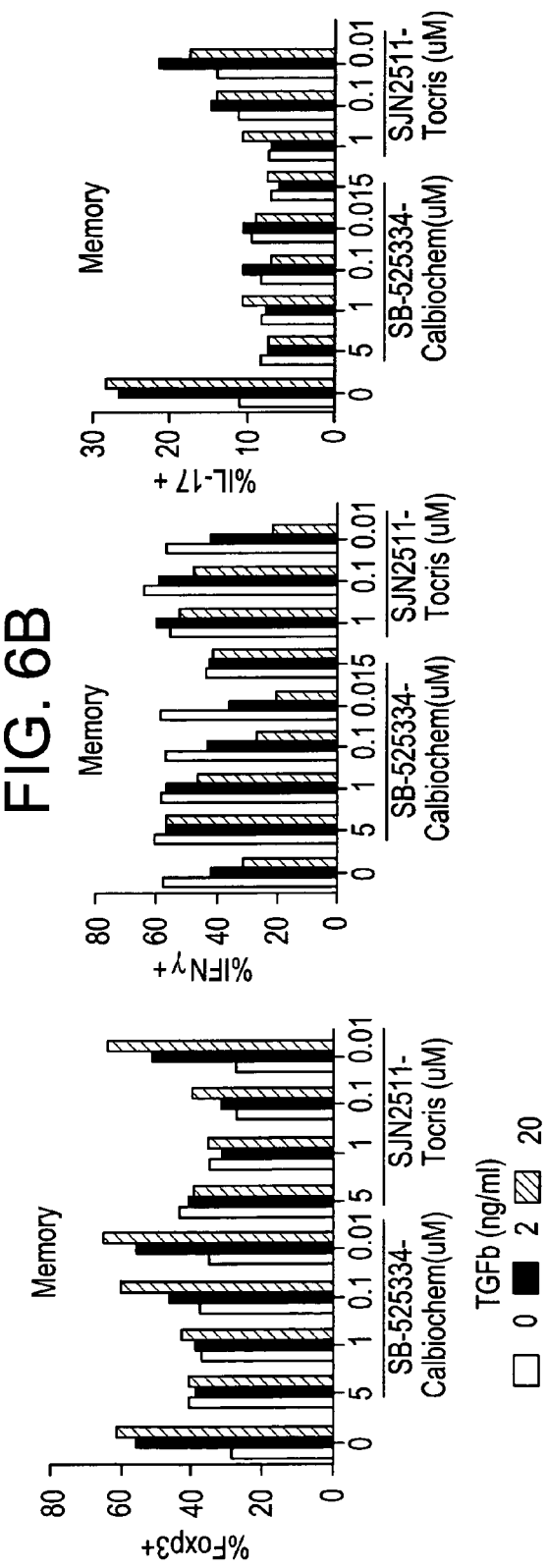
FIG. 6A Naive
FIG. 6B Memory

1

METHODS OF MODULATING TGFβ SIGNALING

The present application claims the benefits of U.S. Provisional Application Ser. No. 61/461,857, filed Jan. 24, 2011, under 35 U.S.C. §119(e).

GOVERNMENT SUPPORT

The research leading to the present inventions was funded in part by Grant No R21AI087973-02 from the National Institutes of Health. The government may have certain rights in the invention.

FIELD OF THE INVENTION

The present invention relates generally to methods for and compositions useful for modulating TGFβ signaling, such as, for instance reducing or amplifying TGFβ signaling. The invention also provides methods for upregulating and suppressing an immune response, and thereby, methods for treating immune related diseases such as autoimmune diseases.

BACKGROUND OF THE INVENTION

A disintegrin and metalloproteases (ADAMs) belong the metzincin family of metalloproteases that also includes astacins and matrix metalloproteases (MMPs). They are all zinc-dependent metalloproteases. [Reiss, et al. *Semin Cell Dev Biol* (2009) 20, 126-137]. To date 23 human ADAMs have been identified. These are type I transmembrane multidomain proteins that contain a disintegrin and a metalloprotease domain that mediate cell adhesion via their disintegrin domain. Members of this family play important roles in many biological processes including cell-surface proteolysis, and cell-cell or cell-matrix interactions by virtue of their metalloprotease domain. They are major ectodomain sheddases that cleave a variety of cell surface proteins including cytokines, growth factors, receptors, as well as components of the extracellular matrix releasing soluble proteins. [White, *Curr Opin Cell Biol* (2003) 15, 598-606] This proteolysis can have multiple functional roles including the release of active peptides from proproteins for autocrine or paracrine signaling (e.g. TNFβ or EGFR ligands), soluble factors that act as antagonists to downregulate signaling, or intracellular proteins that act as transcription factors or indirectly modulate signaling pathways. Also, shedding has emerged as an important mechanism to decrease selective proteins from the cell surface and to inactivate receptors that could potentially act as decoys that sequester soluble ligands. [Reiss, et al. *Semin Cell Dev Biol* (2009) 20, 126-137; White, *Curr Opin Cell Biol* (2003) 15, 598-606]

ADAMs have been implicated in health and disease. They play critical role during fertilization, and are also important for cardiovascular and central nervous system development. They have been associated with autoimmune, inflammatory diseases and cancer progression when dysregulated. [Reiss, et al. *Semin Cell Dev Biol* (2009) 20, 126-137]

ADAM12, also called metrin alpha, is a member of the ADAM family of proteases. [Gilpin, et al. *J Biol Chem* (1998) 273, 157-166] The ADAM12 gene encodes two alternatively spliced transcripts; a long membrane-bound form that has the same structure as a typical ADAM protein (ADAM12-L) and a shorter secreted form that lacks the transmembrane and the cytoplasmic domains (ADAM12-S). [Gilpin, et al. *J Biol Chem* (1998) 273, 157-166] ADAM12-L consists of an amino-terminal secretion signal, prodomain, metalloprotease, disintegrin-like, cysteine-rich, epidermal-growth factor-like, transmembrane and cytoplasmic domains. Functionally, the signal peptide directs ADAM12 to the secretory pathway; the prodomain maintains the protease region in a latent form through cysteine switch mechanism. [Gilpin, et al. *J Biol Chem* (1998) 273, 157-166] The cytoplasmic domain contains several motifs involved in protein-protein interactions for intracellular signaling like SH3-containing domains. Deletion of the C-terminal amino acids accelerates the export of ADAM12 to the cell surface suggesting the presence of a retention signal in the cytoplasmic domain that functions as a limiting factor for the export of the protein from the ER. [Cao, et al. *J Biol Chem* (2002) 277, 26403-26411] ADAM12 is only active as a protease when the prodomain is cleaved. [Loechel, et al. *J Biol Chem* (1998) 273, 16993-16997] In fact, ADAM12 that lacks the prodomain is the predominant form at the cell surface. [Cao, et al. *J Biol Chem* (2002) 277, 26403-26411] Mutating the α-helical region in the prodomain (proline for leu73) results in retention of ADAM12 in the ER and lack of its proteolytic processing. [Cao, et al. *J Biol Chem* (2002) 277, 26403-26411] ADAM12 is synthesized in the ER and matures in the golgi compartment.

ADAM12 is expressed in mesenchymal cells and is lost in adult muscle. It reappears during tissue regeneration. ADAM12 knockout mice were viable and fertile with 30% embryonic lethality. Knockout and transgenic mice implicated ADAM12 in myogenesis [Yagami-Hiromasa, et al. *Nature* (1995) 377, 652-656] and adipocyte differentiation although the phenotype was mild with ADAM12 knockout mice is leaner than their control littermates with abnormalities in their brown adipose tissue with a reduction in the number of adipocytes. [Kawaguchi, et al. *Am J Pathol* (2002) 160, 1895-1903]

ADAM12 is implicated in a variety of diseases including muscular dystrophies, Alzheimer's (where two single nucleotide polymorphisms in the ADAM12 gene were identified and significantly associated with late-onset Alzheimer's disease, [Harold, et al. *Am J Med Genet B Neuropsychiatr Genet* (2007) 144B, 448-452] and processes characterized by excessive growth including pregnancy where it is highly expressed in human placenta and reach high concentrations in maternal serum from the first trimester, and is currently being evaluated as a prenatal marker for the detection of chromosomal abnormalities as ADAM12-S serum concentrations are significantly reduced in trisomy-18 [Spencer, et al. *J Matern Fetal Neonatal Med* (2007) 20, 645-650] and trisomy-21 pregnancies [Toning, et al. *Reprod Biol Endocrinol* 8, 129], cardiac hypertrophy [Wang, et al. *Circulation* (2009) 119, 2480-2489] but most importantly in cancer being upregulated in a variety of human tumors. [Kveiborg, et al. *Int J Biochem Cell Biol* 2008 40, 1685-1702] It is suggested to be involved in the development and progression of tumors possibly due to stimulating growth factor responses by a mechanism called "shedding" that releases active proteins, and also through its adhesion activity. Interestingly, ADAM12 was also linked to CNS inflammation by its upregulation in the spinal cords of mice with EAE, being expressed primarily by infiltrating T cells. [Toft-Hansen, et al. *J Immunol* 2004 173, 5209-5218] However, not much is known about the function of this gene in T cells and more specifically in Th17 cells especially that increased levels of IL-17 transcripts were associated with multiple sclerosis and the severity of EAE in mice.

It was shown that ADAM12 regulates TGFβ signaling through its interaction with TGFbRII where the two proteins localize to areas near the cell surface. [Atfi, A. et al. *J Cell Biol* (2007) 178, 201-208] ADAM12 increases the steady state level of TGFRII and decreases its ubiquitination and turnover, resulting in increased SMAD2 and SMAD3 phosphorylation and decreased SMAD7. ADAM12 does not maintain transcriptional activity after TGF-β removal indicating a positive feedback mechanism between TGF signaling and ADAM12. [Atfi, A. et al. *J Cell Biol* (2007) 178, 201-208] In support of this notion, it was shown that TGFβ signaling causes derepression of the ADAM12 gene in a SMAD2/3 dependent manner, through inducing the proteasomal degradation of SnoN, the repressor that negatively regulates ADAM12. [Solomon, et al. *J Biol Chem* 285, 21969-21977] Overexpression and silencing of SnoN alters the magnitude of ADAM12 induction by TGFβ. [Solomon, et al. *J Biol Chem* 285, 21969-21977] However, still not much is known regarding the regulation of ADAM12, possible through hormones, cytokines and growth factors.

TGFβ is a secreted protein that exists in three isoforms called TGFβ1, TGFβ2, and TGFβ3. It was also the original name for TGFβ1, which was the founding member of this family, and the predominant form expressed in the immune system. TGFβ is synthesized as a precursor made of a dimer of mature TGFβ, that is non-covalently linked to a dimer of latency associated peptide (LAP) in a complex called small latent complex (SLC). LAP in SLC binds one molecule of latent TGFβ binding protein (LTBP) to form a bigger complex called large latent complex (LLC). LLC is released from the cell and needs further processing to deliver active TGFβ. [Todorovic, et al. *Int J Biochem Cell Biol* (2005) 37, 38-41]

TGFβ resists proteolysis and extreme pH conditions, and so the most common laboratory way to activate TGFβ is by treating media or biological fluids with an acid that lowers the pH to 2.0 for a short period of time. [Taylor, *J Leukoc Biol* (2009) 85, 29-33] Alternatively, incubating culture media for 10 minutes at 80° C., or by freezing and thawing can activate TGFβ. The in vivo activation mechanisms are still speculative, but could involve proteases that cleave LTBP and frees LAP in LLC from the matrix. LAP now can be further cleaved by proteases or through conformational changes to release mature TGFβ. [Taylor, *J Leukoc Biol* (2009) 85, 29-33]

There are different groups of TGFβ Receptors. The first one binds LAP as part of LLC or SLC and includes integrins αvβ6 and αvβ8 [Wipff, et al. *Eur J Cell Biol* (2008) 87, 601-615], thrombospondin-1 and neuropilin [Glinka, et al. *J Leukoc Biol* 2008 84, 302-310], as well as tissue matrix proteins that bind LTBP. These surface receptors of LAP allow the cells to hold latent TGFβ on their surface for autocrine or paracrine signaling of active TGFβ. This is suggested as one mechanism by which regulatory T cells suppress the activity of other T cells. [Glinka, et al. *J Leukoc Biol* 2008 84, 302-310] Tregs express LAP on their membrane surface [Chen, et al. *J Immunol* (2008) 180, 7327-7337] and LAP+ Tregs produce active TGFβ. Neuropilin is so far the identified binding protein for LAP on Tregs and could be the way by which Tregs activates TGFβ and delivers it to other T cells to suppress immune responses.

The second group of receptors binds active TGFβ. [Massague, *Mol Cell* (2008) 29, 149-150] This comprises TGF-βRI, TGFβRII, and TGFβRIII. Type III acts as a sink, mopping up active TGFβ; however, when bound on the cell surface, it facilitates TGFβ binding to RII. Active TGFβ binds RII, which recruits and phosphorylates RI. An activation complex is formed and made of 2 pairs of RI and RII, with each pair binds one of the two chains of active TGFβ. [Massague, *Mol Cell* (2008) 29, 149-150] Phosphorylated RI then recruits and phosphorylates a receptor regulated SMAD (R-SMAD) like SMAD2 and SMAD3. R-SMAD then binds to SMAD4 and forms a heterodimeric complex that then enters the nucleus where it acts as a transcription factor for many genes. SMAD pathway is the canonical signaling pathway that TGFβ family members signal through to target genes.

TGFβ is a pleiotropic cytokine involved in various physiological and pathological processes such as carcinogenesis and embryogenesis. [Blobe, et al. *N Engl J Med* (2000) 342, 1350-1358] In the immune system, recent studies have defined TGFβ as a critical regulator of thymic T cell development, an important player in T cell homeostasis, peripheral tolerance to self-antigens to limit inflammatory diseases and in T cell differentiation particularly Th17 and Tregs. [Li, et al. *Cell* (2008) 134, 392-404]

The induction of Th17 and Tregs by TGFβ is mutually exclusive meaning that the conditions that favor Th17 inhibits Tregs and vice versa. During homeostasis, the development of induced Tregs is favored in the TGFβ-rich gut-associated lymphoid tissue (GALT) promoted by retinoic acid, a metabolite of dietary vitamin A produced by dendritic cells in the intestinal mucosa. When pathogenic bacteria activate DCs, the latter produce inflammatory cytokines, do not metabolize vitamin A to retinoic acid, and therefore TGFβ-induced differentiation of naïve T cells is diverted away from Tregs to Th17 cells. [Bettelli, et al. *Nature* 2006) 441, 235-238; Mangan, et al. *Nature* (2006) 441, 231-234]

The importance of TGFβ in T cell lineage development is supported by evidence that mice with αvβ8 (activator of TGFβ) knocked out on their dendritic cells suffer from autoimmunity and colitis. [Travis, et al. *Nature* (2007) 449, 361-365] There is a significant loss in the ability of these DCs to induce activation of Treg, and that was reversed by the addition of active TGFβ. [Travis, et al. *Nature* (2007) 449, 361-365] The fate of Th17 cells was not examined in this study, but one may speculate that αvβ8 mice have high levels of IL-17 producing cells, which potentially contribute to the immunopathology seen in these mice.

Gruel et al., *BMC Research Notes* 2009; 2:193 teach that ADAM12 induces a permanent response to TGFβ in some cells. Wewer et al., WO2005/111626 teach a method, an assay and a kit for providing an indication of abnormal cell function based upon change in serum ADAM12 concentration. ADAM12 was described as an overall general marker for abnormal cell function, and an important indicator of fetal chromosomal disease and placenta function, e.g. Downs's syndrome, trisomy 18, preeclampsia, and Turner syndrome in both first and second trimester.

Bosch et al., WO2006/014903 teach that ADAM12L is overexpressed on the surface of cancer cells compared to normal tissues and therefore is a therapeutic target for treating cancer. Modulators of ADAM12, highly expressed in cancerous tissue compared to normal tissue are indicated as useful for treating certain proliferative disorders such as cancer and psoriasis.

Suonpaa et al., WO2008/119882 teach epitopes of ADAM12 and to binding agents specific to those epitopes. Also, Suonpaa et al. teach methods of detecting ADAM12 in a biological sample as well as diagnostic and screening methods using these binding agents.

SUMMARY OF THE INVENTION

The present invention is based in part upon the discovery that a disintegrin and metalloprotease, ADAM, such as ADAM12, a protease specifically expressed on both ex vivo isolated Th17 and induced regulatory T cells (iTreg) cells and amplifies TGFβ signals in these T cell subsets.

In a first aspect, the invention provides methods of identifying the presence of or quantifying the amount of one or more of T helper (Th) cells and iTreg cells present in a sample such as a biological sample by identifying the presence of an ADAM or the amount of an ADAM present in a sample. In some embodiments, the Th cells are Th17 cells or iTregs. In other embodiments the ADAM is ADAM12. In some embodiments the present invention takes advantage of the discovery that ADAM12 expression is a biomarker for human Th17 cells and iTregs that secrete IL-17. In some embodiments the ADAM such as ADAM12 is detected or quantified in a sample using an antibody such as a labeled antibody.

In a second aspect, the present invention provides methods for increasing signaling of a TGF such as TGFβ by increasing the biological activity or expression of an ADAM or by administering an ADAM, such as, for instance, ADAM12. In some instances, the increasing the biological activity or expression of an ADAM may be effected by administering an agent that stimulates expression of an ADAM, such as, for instance, a small molecule, an antibody, a DNA or RNA, or a genetic construct, such as for instance might be administered by standard gene therapy techniques. In some instances, the signaling is increased in helper T cells, such as, for instance, Th17 cells or iTregs.

In a third aspect, the present invention provides methods for decreasing signaling of a TGF such as TGFβ by decreasing the biological activity or expression of an ADAM or by administering an agent that functions to inhibit the expression or biological activity of an ADAM, such as, for instance, ADAM12. In some instances, the signaling is decreased in helper T cells, such as, for instance, Th17 cells or iTregs. In some embodiments, the agent that functions to inhibit the expression or biological activity of an ADAM, such as, for instance, ADAM12, is a small molecule while in other embodiments the agent that functions to inhibit the expression or biological activity of an ADAM, such as, for instance, ADAM12, is an antibody or an interfering RNA or DNA molecule.

In a fourth aspect, the present invention provides methods for inhibiting an immune response. The methods for inhibiting an immune response feature increasing the biological activity or expression of an ADAM or administering an ADAM, such as, for instance, ADAM12. In some instances, the increasing the biological activity or expression of an ADAM may be effected by administering an agent that stimulates expression of an ADAM, such as, for instance, a small molecule, an antibody, a DNA or RNA, or a genetic construct, such as for instance might be administered by standard gene therapy techniques. In some instances, the signaling is increased in helper T cells, such as, for instance, Th17 cells or iTregs. The methods for inhibiting an immune response are performed by increasing signaling of a TGF such as TGFβ.

In a fifth aspect, the present invention provides methods for treating a disease characterized, all or in part, or caused, all or in part, by an immune response. The methods for treating a disease characterized, all or in part, or caused, all or in part, by an immune response feature increasing the biological activity or expression of an ADAM or administering an ADAM, such as, for instance, ADAM12. In some instances, the increasing the biological activity or expression of an ADAM may be effected by administering an agent that stimulates expression of an ADAM, such as, for instance, a small molecule, an antibody, a DNA or RNA, or a genetic construct, such as for instance might be administered by standard gene therapy techniques. In some instances, the signaling is increased in helper T cells, such as, for instance, Th17 cells or iTregs. The methods for treating a disease characterized, all or in part, or caused, all or in part, by an immune response are performed by increasing signaling of a TGF such as TGFβ. The disease characterized, all or in part, or caused, all or in part, by an immune response may be, for instance, excessive inflammation, an autoimmune disease such as, for instance, rheumatoid arthritis, inflammatory bowel disease (IBD), multiple sclerosis (MS), or psoriasis, allergic diseases such as asthma or graft-versus-host disease such as may occur after transplantation or chronic diseases where inflammation contributes such as cardiovascular diseases, chronic obstructive lung disease (COPD), type II diabetes, stroke, Alzheimer's disease and some forms of cancer.

In a sixth aspect, the present invention provides methods for stimulating an immune response. The methods for stimulating an immune response may be effected by decreasing the biological activity or expression of an ADAM or by administering an agent that functions to inhibit the expression or biological activity of an ADAM, such as, for instance, ADAM12. In some instances, the signaling is decreased in helper T cells, such as, for instance, Th17 cells or iTregs. In some embodiments, the agent that functions to inhibit the expression or biological activity of an ADAM, such as, for instance, ADAM12, is a small molecule while in other embodiments the agent that functions to inhibit the expression or biological activity of an ADAM, such as, for instance, ADAM12, is an antibody or an interfering RNA or DNA molecule.

In a seventh aspect, the present invention provides methods for treating a disease that may be successfully treated, all or in part, by stimulating an immune response. The methods for treating a disease that may be successfully treated, all or in part, by stimulating an immune response feature decreasing the biological activity or expression of an ADAM or administering an agent that functions to inhibit the expression or biological activity of an ADAM, such as, for instance, ADAM12. In some instances, the signaling is decreased in helper T cells, such as, for instance, Th17 cells or iTregs In some embodiments, the agent that functions to inhibit the expression or biological activity of an ADAM, such as, for instance, ADAM12, is a small molecule while in other embodiments the agent that functions to inhibit the expression or biological activity of an ADAM, such as, for instance, ADAM12, is an antibody or an interfering RNA or DNA molecule. The methods for treating a disease that may be successfully treated, all or in part, by stimulating an immune response are performed by decreasing signaling of a TGF such as TGFβ. The disease that may be successfully treated, all or in part, by stimulating an immune response may be, for instance, a cancer, a neoplasm, a viral infection, a bacterial infection or a fungal infection.

In an eighth aspect, the present invention provides methods to identify agents such as small molecules, proteins and antibodies that may inhibit an immune response or that may increase or upregulate a TGF, such as TGFβ, signaling. The invention identifies a novel target that can be manipulated to regulate an immune response. Agents such as small molecules, proteins and antibodies that may inhibit an immune response or that may increase or upregulate a TGF, such as TGFβ, signaling, may be identified by standard assay techniques known in the art as applied to identify those agents that increase the biological activity or expression of an ADAM such as ADAM12. Agents so identified may be useful to treat a disease characterized, all or in part, or caused, all or in part, by an immune response. The disease characterized, all or in part, or caused, all or in part, by an immune response may be, for instance, excessive inflammation, an autoimmune disease such as, for instance, inflammatory bowel disease (IBD), multiple sclerosis (MS), lupus, or psoriasis, or graft-versus-host disease such as may occur after transplantation. As such, these methods are also methods of screening for therapeutic agents effective to inhibit or downregulate an immune response and to treat a disease characterized, all or in part, or caused, all or in part, by an immune response.

In an ninth aspect, the present invention provides methods to identify agents such as small molecules, proteins and antibodies, that may stimulate an immune response or that may inhibit or downregulate a TGF, such as TGFβ, signaling. The invention identifies a novel target that can be manipulated to regulate an immune response. Agents such as small molecules, proteins and antibodies that may stimulate an immune response or that may decrease or downregulate a TGF, such as TGFβ, signaling, may be identified by standard assay techniques known in the art as applied to identify those agents that decrease the biological activity or expression of an ADAM such as ADAM12. Agents so identified may be useful to treat a disease that may be successfully treated, all or in part, by stimulating an immune response. The disease that may be successfully treated, all or in part, by stimulating an immune response may be, for instance, a cancer, a neoplasm, a viral infection, a bacterial infection or a fungal infection. As such, these methods are also methods of screening for therapeutic agents effective to stimulate or upregulate an immune response and to treat a disease that may be successfully treated, all or in part, by stimulating an immune response.

In a tenth aspect, the present invention provides pharmaceutical compositions that may inhibit or downregulate an immune response, that may increase or upregulate a TGF, such as TGFβ, signaling, and that may be effective to treat a disease characterized, all or in part, or caused, all or in part, by an immune response. The disease characterized, all or in part, or caused, all or in part, by an immune response may be, for instance, excessive inflammation, an autoimmune disease such as, for instance, inflammatory bowel disease (IBD), multiple sclerosis (MS), lupus, or psoriasis, or graft-versus-host disease such as may occur after transplantation. The pharmaceutical compositions contain one or more agents effective to increase the biological activity or expression of an ADAM or an ADAM, such as, for instance, ADAM12, along with a pharmaceutically acceptable carrier. In some instances, the pharmaceutical compositions may contain an agent that stimulates expression of an ADAM, such as, for instance, a small molecule, an antibody, a DNA or RNA, or a genetic construct, such as for instance might be administered by standard gene therapy techniques, along with a pharmaceutically acceptable carrier.

In an eleventh aspect, the present invention provides pharmaceutical compositions that may stimulate or upregulate an immune response, that may decrease or downregulate a TGF, such as TGFβ, signaling, and that may be effective to treat a disease that may be successfully treated, all or in part, by stimulating an immune response, such as, for instance, a cancer, a neoplasm, a viral infection, a bacterial infection or a fungal infection. The pharmaceutical compositions contain one or more agents that function to inhibit the expression or biological activity of an ADAM, such as, for instance, ADAM12. In some embodiments, the agent that functions to inhibit the expression or biological activity of an ADAM, such as, for instance, ADAM12, is a small molecule while in other embodiments the agent that functions to inhibit the expression or biological activity of an ADAM, such as, for instance, ADAM12, is an antibody or an interfering RNA or DNA molecule. The compositions containing the agents that function to inhibit the expression or biological activity of an ADAM, such as, for instance, ADAM12, may further contain a pharmaceutically effective carrier.

In a twelfth aspect the present invention features a vaccine effective to modulate an immune response that may contain an ADAM such as, for instance, ADAM12, or a fragment thereof.

BRIEF DESCRIPTION OF THE DRAWINGS

FIG. 1 depicts identification of a metalloprotease expressed on memory CCR6+ cells. (A) CD4$^+$ T cells isolated from human PBMCs were stained with CCR6-biotin and CCR5-phycoerythrin and sorted into four T cell subsets: R6+R5−, R6+R5+, R6−R5+, and R6−R5−. (B) T-cell subsets identified in (A) were TCR activated for 24 hrs and ADAM12 levels are shown from the microarray analysis. (C) Levels of ADAM12, IL-17 and RORgt from different T cell subsets (from A and in mCCR6+ and mCCR6−) 24 hrs post TCR activation as determined by qrt-PCR. (D) Kinetics of ADAM12 levels in mCCR6+ at different time points before and after TCR stimulation (d, days). (E) Levels of ADAM12, ADAM19, and ADAM22 from different T cell subsets (from A) 24 hrs post TCR activation as determined by qrt-PCR. One experiment representative of three or more donors is shown.

FIG. 6 represents that TGFβRI inhibitors abolish the effect of TGFβ on TGFβ responsive genes in Naïmd ve and mCCR6+ T cells. Naïve (A) or Memory (B) T cells were stimulated through TCR and pretreated for 60 min with TGFβ inhibitors at the different indicated concentrations (0.01-5 uM) before the addition of TGFβ (2&20 ng/ml). Cells were stained for Foxp3-Alexa647 on day 3 (A, B) and for IFNγ-pecy7 and IL-17-percp-cy5.5 on day 6 after re-stimulation with P+I (B).

DETAILED DESCRIPTION OF THE INVENTION

Figure 2A:
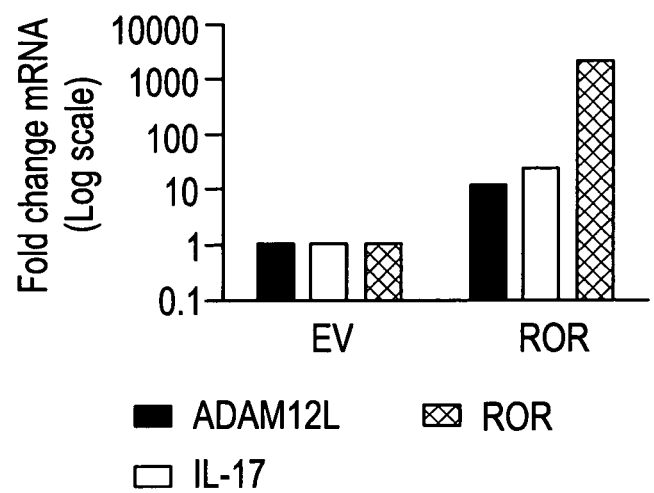
FIG. 2 represents expression of ADAM12 in ROR-transduced and ex-vivo isolated Th17 cells. (A) Levels of ADAM12, IL-17 and ROR from ROR-transduced (ROR) or vector control (EV) T cells as determined by qrt-PCR. Cells were expanded in culture for 7-10 days before sorting for ROR+ cells or EV+ cells and then RNA was collected post sort. (B) Ex-vivo isolation of Th17 cells from ROR-transduced T cells. Cells were activated as described in materials and methods, and then surface stained for IL-17-PE. They were then sorted into ROR+IL-17+ and ROR+IL-17−. Cells from each subset were flash frozen for qrt-PCR performed using ADAM12 and IL-17 primers. (C) Representative T cell subset staining from normal donor using CD45RO-Fitc and CD25-PE antibodies. Memory T cells (TM) defined as CD45RO+CD25− were further sorted into CCR6+ and CCR6− subsets, followed by activation and surface staining using IL-17− PE antibody. Levels of ADAM12, IL-17 and ROR were determined in all sorted T cell subsets 24 hrs post TCR activation using qrt-PCR. (D) Levels of ADAM12, ADAM19, and ADAM22 from different T cell subsets (from C) 24 hrs post stimulation as determined by qrt-PCR. One experiment representative of three donors is shown.

Various terms are used in the specification, which are defined as follows:

As used herein a "small organic molecule" is an organic compound (or organic compound complexed with an inorganic compound (e.g., metal)) that has a molecular weight of less than 3 kilodaltons, and preferably less than 1.5 kilodaltons. An "agent" of the present invention is preferably a small organic molecule.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

In a specific embodiment, the term "about" means within 20%, preferably within 10%, and more preferably within 5%.

In accordance with the present invention there may be employed conventional molecular biology, microbiology, and recombinant DNA techniques within the skill of those in the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (See, Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5.times.SSC, 0.1% SDS, 0.25% milk, and no formamide; or 30% formamide, 5.times.SSC, 0.5% SDS). Moderate stringency hybridization conditions correspond to a higher T.sub.m, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA. DNA:RNA. DNA:DNA. For hybrids of greater than 100 nucleotides in length, equations for calculating $T_m$ have been derived (See, Sambrook et al., supra, 9.50-0.51). For hybridization with shorter nucleic acids, i.e., oligonucleotides, the position of mismatches becomes more important, and the length of the oligonucleotide determines its specificity (See, Sambrook et al., supra, 11.7-11.8). Preferably a minimum length for a hybridizable nucleic acid is at least about 18 nucleotides; preferably at least about 36 nucleotides; and more preferably the length is at least about 48 nucleotides. Such nucleic acids can be used as primers or nucleic acid probes for the nucleic acids encoding the translocation promoting agents of the present invention.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667 (1987)).

Accordingly, the term "sequence similarity" in all its grammatical forms refers to the degree of identity or correspondence between nucleic acid or amino acid sequences of proteins that do not share a common evolutionary origin (See, Reeck et al., Cell 50:667 (1987)). However, in common usage and in the instant application, the term "homologous," when modified with an adverb such as "substantially," may refer to sequence similarity and not a common evolutionary origin.

In a specific embodiment, two DNA sequences are "substantially homologous" or "substantially similar" when at least 50% (preferably at least 75%, and most preferably at least 90 to 95%) of the nucleotides match over the defined length of the DNA coding sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program with the default parameters.

The term "corresponding to" is used herein to refer similar or homologous sequences, more preferably substantially similar or substantially homologous sequences, whether the exact position is identical or different from the molecule to which the similarity or homology is measured. The term "corresponding to" refers to the sequence similarity, and not the numbering of the amino acid residues or nucleotide bases.

The term "disease characterized, all or in part, or caused, all or in part, by an immune response" includes, for example, the following diseases: all autoimmune diseases (eg. Rheumatoid arthritis, Psoriasis, Multiple sclerosis, ulcerative colitis, Crohn's disease, type I juvenile diabetes, SLE), allergic diseases (e.g. asthma, atopic dermatitis, allergic rhinitis, food allergies), transplantation rejection and graft-versus-host-disease after solid organ or bone marrow transplantation respectively, various cancers where TGFβ signaling is involved in promoting tumors such as breast and lung cancer, chronic diseases that are caused or promoted by inflammation (e.g. atherosclerosis, congestive heart failure, type II diabetes, chronic obstructive pulmonary disease (COPD), Alzheimer's disease, fibrosis, stroke, pancreatitis), and during chronic infections that cause excessive immune activation such as HIV infection, severe forms of influenza, tuberculosis, shingles, CMV infections, bacterial infections that can cause septic shock.

Effect of ADAM12 on TGFβ Signaling

ADAM12 functions to amplify TGFβ signaling. Small molecules or biologicals that upregulate either expression or enzymatic activity of ADAM12 amplify TGFβ signals. This results in suppression of IL-17/IL-22 secretion by Th17 cells and conversely promotes regulatory T cells that suppress immune responses. This approach may be utilized in inhibiting excessive inflammation, treatment in auto-immune diseases including IBD, MS and Psoriasis and potentially preventing graft-versus-host disease after transplantation.

Small molecules or biologicals or specific antibodies that downregulate or block either ADAM12 expression or disrupt its enzymatic activity on cell surface or in soluble forms reduce TGFβ signals. This in turn upregulates inflammatory responses by Th17 cells and reduces immune suppression. This approach is useful in developing vaccines or in amplifying immune responses to cancer and bacterial or fungal infections.

TGFβ

TGFβ is a pleiotropic cytokine that can induce the differentiation of both the suppressor induced regulatory T cells (iTregs) and the proinflammatory Th17 cells. How TGFβ signaling is regulated in these opposing functions is not known. The metalloprotease ADAM12, through microarray analysis, was identified to be specifically upregulated in both human memory CCR6+ T cells that secrete IL-17 or have Treg phenotype, and Tregs. ADAM12 as described above has been implicated in TGFβ signaling. Ectopic expression of ADAM12 in human naïve T cells resulted in upregulation of the transcription factor Foxp3 and decreased IFNγ production. The changes induced by ADAM12 in primary cells, were blocked by specific inhibitors of TGFβ signal transduction. In contrast, silencing ADAM12 in human memory CCR6+ cells reduced expression of Foxp3 and increased the secretion of IL-17 and IL-22 cytokines. Moreover, ADAM12 knockdown in CCR6+ T cells reduced SMAD2 and SMAD3 phosphorylation in response to TGFβ signaling. In a reporter assay for TGFβ-signaling, it was demonstrated that ADAM12 does not activate latent TGFβ. Together, these data suggest that ADAM12 modulates TGFβ signaling by modulating either cell surface expression or conformation of TGFβ receptors.

A subset of human T cells called, Th17 cells have been shown to be important in protection against several bacterial and fungal infections. Th17 cells are also implicated in the development of several autoimmune diseases including inflammatory bowel diseases (IBDs). The Th17 cell differentiation from naïve precursors require proinflammatory cytokines such as IL-6, IL-1b, and IL-21, in addition to TGFβ. Almost all human Th17 cells also express the chemokine receptor CCR6.

Conversely, Treg cells have suppressive functions that curb inflammation by suppressing the activation of lymphocytes and inflammation. Tregs are also divided into thymus-derived (bona fide Tregs) and induced Tregs (iTregs), which differentiate from naïve T cells through TGFβ signaling. More recently a portion of iTregs were shown to also express CCR6 and IL-17. These regulatory cells are also endowed with a proinflammatory cytokine.

Because differentiation of both Th17 cells and iTregs require TGFβ signaling, it may be that the same cytokine can induce T cell subsets with opposing functions. Treatment of TCR-activated naïve CD4+ T cells with TGFβ alone induces the expression of both RORgt and Foxp3, which are required for development of Th17 and Treg lineages respectively. Paradoxically, TGFβ alone can also suppress RORgt activity through induction of Foxp3 and inhibit Th17 cell differentiation IL-17. Therefore, understanding the role of TGFβ in maintaining the equilibrium between Treg and Th17 cells could be critically important in regulating inflammation and preventing the development of autoimmune diseases.

The discovery of metalloprotease ADAM12, specifically expressed on CCR6+ Th17 and Treg cells, indicates that this protein has important function in these inflammatory and suppressor subsets. ADAM12 was expressed in naïve T cells and found to amplify TGFβ responses as determined by increased Foxp3 and decreased IFNγ production. Conversely, silencing ADAM12 in CCR6+ cells impaired TGFβ signals. The effects of ADAM12 overexpression were also abrogated by inhibitors of TGFβ receptor signaling. This finding suggested that ADAM12 amplifies TGFβ at the receptor level and not through downstream signaling. The tuning of TGFβ signals in CCR6+ cells is critically important in regulating TGFβ function in regulatory versus inflammatory T cell differentiation.

Administration of the Therapeutic Compositions of the Present Invention

According to the present invention, the component or components of a therapeutic composition of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In some instances, the components or composition are administered to prevent or treat a disease characterized by or caused all or in part by an immune response such as an autoimmune disease or graft versus host disease and are introduced by injection into the blood. In another embodiment, the therapeutic components or composition can be delivered in a vesicle, in particular a liposome (See, Langer, *Science* 249: 1527-1533 (1990); Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, the therapeutic compound can be delivered in a controlled release system. For example, an antibody may be administered using intravenous infusion, an implantable osmotic pump, a transdermal patch, liposomes, or other modes of administration. In one embodiment, a pump may be used (See, Langer, supra; Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of a therapeutic target, e.g., the brain, thus requiring only a fraction of the systemic dose (See, e.g., Goodson, in Medical Applications of Controlled Release, supra, vol. 2, pp. 115-138 (1984)). Other controlled release systems are discussed in the review by Langer, *Science* 249:1527-1533 (1990).

Thus, a therapeutic composition of the present invention can be delivered by intravenous, intraarterial, intraperitoneal, intramuscular, or subcutaneous routes of administration. Alternatively, the therapeutic compositions, properly formulated, can be administered by nasal or oral administration. A constant supply of the therapeutic composition can be ensured by providing a therapeutically effective dose (i.e., a dose effective to induce metabolic changes in a subject) at the necessary intervals, e.g., daily, every 12 hours, etc. These parameters will depend on the severity of the disease or condition being treated, other actions, such as diet modification, that are implemented, the weight, age, and sex of the subject, and other criteria, which can be readily determined according to standard good medical practice by those of skill in the art.

A subject in whom administration of the therapeutic composition is an effective therapeutic regiment is preferably a human, but can be a primate with a related immune related condition. Thus, as can be readily appreciated by one of ordinary skill in the art, the methods and pharmaceutical compositions of the present invention are particularly suited to administration to a number of animal subjects including humans.

Transgenic Vectors and Effecting Expression

In one embodiment, a gene encoding a therapeutic compound can be introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus macrophage can be specifically targeted. Examples of particular vectors include, but are not limited to, an attenuated adenovirus vector, such as the vector described by Stratford-Perricaudet et al. *J. Clin. Invest.* 90:626-630 (1992)), and a defective adeno-associated virus vector (Samulski et al., *J. Virol.* 61:3096-3101 (1987); Samulski et al., *J. Virol.* 63:3822-3828 (1989)).

In another embodiment the gene or antigene can be introduced in a retroviral vector, e.g., as described in Anderson et al., U.S. Pat. No. 5,399,346; Mann et al., 1983, *Cell* 33:153; Temin et al., U.S. Pat. No. 4,650,764; Temin et al., U.S. Pat. No. 4,980,289; Markowitz et al., 1988, *J. Virol.* 62:1120; Temin et al., U.S. Pat. No. 5,124,263; International Patent Publication No. WO 95/07358, published Mar. 16, 1995, by Dougherty et al.; and Kuo et al., 1993, *Blood* 82:845.

Targeted gene delivery is described in International Patent Publication WO 95/28494, published October 1995.

Alternatively, the vector can be introduced in vivo by lipofection (Felgner, et. al., *Proc. Natl. Acad. Sci. U.S.A.* 84:7413-7417 (1987); see Mackey, et al., Proc. Natl. Acad. Sci. U.S.A. 85:8027-8031 (1988); Felgner and Ringold, *Science* 337:387-388 (1989)). Lipids may be chemically coupled to other molecules for the purpose of targeting (See, Mackey, et. al., supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (See, e.g., Wu et al., *J. Biol. Chem.* 267:963-967 (1992); Wu and Wu, *J. Biol. Chem.* 263:14621-14624 (1988); Hartmut et al., Canadian Patent Application No. 2,012,311, filed Mar. 15, 1990).

Example 1

Materials and Methods

T Cell Purification

Peripheral blood mononuclear cells from healthy individuals (NY Blood center) were prepared using FICOLL-PAQUE PLUS® (GE Health care). CD4$^+$ T cells were isolated using Dynal CD4 Positive Isolation Kit (Invitrogen) and were >99% pure. CD4$^+$ cells were sorted by flow cytometry (FACSAria; BD Biosciences) on the basis of expression of CD45RO, CCR6 and CD25 for naïve (TN: CD45RO−CD25−), memory T cells (TM: CD45RO+CD25−CCR6+) and Tregs (CD45RO+CD25+). Sorted subsets were >99% pure and were kept at 37° C. and 5% CO2 in Roswell Park Memorial Institute 1640 medium with 10% fetal calf serum.

T Cell Activation and Infection

Sorted CD4$^+$ T cell subsets were stimulated using anti-CD3 and anti-CD28 coated beads or monocyte-derived dendritic cells and OKT3, and maintained in IL-2 containing media. Simultaneously, activated cells were infected with lentiviruses expressing ADAM12-cDNA or shRNAs or mock infected. For intracellular cytokine staining, cells were reactivated for 5 h with Phorbol ester (20 ng/mL; Sigma), ionomycin (500 ng/mL; Sigma), and GOLGISTOP® (Brefeldin A; BD Biosciences) to prevent protein secretion. In the experiments using TGFβRI inhibitors, cells were pre-treated with TGFβRI specific inhibitors, SB-525334 (Calbiochem), and SJN2511 (Tocris bioscience) at the time of activation for 1 hour before the addition of recombinant TGFβ (R&D).

Microaaray Gene Analysis

CD4+ T cells were sorted into 4 subsets based on CCR5 and CCR6 chemokine expression profile, 10$^6$ T cells from each subset (CCR5−CCR6+, CCR5+CCR6+, CCR5−CCR6+, CCR5−CCR6−) were activated by plate-bound anti-CD3 antibody (OKT-3; American Type Culture Collection, Manassas, Va.) and soluble anti-CD28 antibody (1 µg/ml, BD Biosciences, San Diego, Calif.) for 16 hours. Cells were flash frozen and total RNA was extracted and purified using Ribopure (Ambion) RNA isolation at Genus Biosysterns (Genus *Biosysterns*, Northbrook, Ill.). cDNA and cRNA target were prepared and hybridized to Agilent Whole Genome 4×44K arrays. Data was analyzed with Agilent Feature Extraction and GeneSpring GX v7.3.1 software packages.

RNA Isolation and Quantitative PCR

Purified T cells were flash frozen in liquid nitrogen. Total RNA was isolated using RNEASY® isolation kit (Qiagen, Valencia, Calif.) according to the manufacturer's protocol, reverse transcribed into cDNA and quantified using TAQMAN® Cell to CT kit (Applied Biosystems, Carlsbad, Calif.). Taqman primers and probe mixes were purchased from Applied Biosystems, and their IDs are as follows: Human ADAM12L (Hs00185774 µml), ADAM12S (Hs00222216 µml), ROR C (Hs01076112 µml), Foxp3 (Hs00203958 µml), ADAM19 (Hs00224960 µml), ADAM22 (Hs00244640 µml), IL-17F (Hs00369400 µml), IL-17A (Hs99999082 µml) and β-Actin (Hs99999903 µml). Data was acquired and analyzed on ABI 7500 sequence detection system by normalizing Ct values of genes of interest to the Ct values of the housekeeping gene β-Actin.

Cloning of ADAM12 Gene

Human ADAM12 cDNAs (NM_003474 and NM_021641) were purchased from Origene (Rockville, Md.). Both cDNAs have a myc and a Flag tag at the C-terminus. The ORF of soluble ADAM 12 (NM_021641) was subcloned into a HIV-derived vector expressing RFP as a marker gene (Unutmaz et al. 1999) in frame using EcoRI and SacII sites. The ORF of full length human ADAM 12 (NM_003474) was amplified by PCR using the primers:
5'forward: GCCCGCGGGCATTGCCATGGCAGCGCGC-CCGCTG (SEQ ID NO:1)
3'reverse: GACCGCGGCCGGCCGTTTAAACCT-TATCGTCGTC (SEQ ID NO:2)

All constructs were sequence confirmed. Lentiviruses expressing ADAM12 were generated and viral titers were measured as described elsewhere (Unutmaz et. 1999).

Silencing of ADAM12 Expression in T Cells

ADAM12 shRNA-expressing lentiviral vectors with puromycin as a selection marker in primary T cells were purchased from Sigma( ). 5 different ADAM12 shRNAs targeting different sequences of the gene were tested. Two of them showed efficient knock down of ADAM12. Lentiviral particles were generated on 293T cells according to the manufacturer's instructions (Sigma), and viral titers were estimated on primary T cells using puromycin. Activated memory T cells were transduced with ADAM12 shRNAs and maintained in IL-2 containing RPMI media.

Staining and FACS Sorting Analysis

Cells were stained with corresponding antibodies, as previously described (Kyra Plos pathogen 2007). For intracellular staining, Fixation and permeabilization were performed using Foxp3 staining Kit (eBioscience) in accordance with the manufacturer's instructions. Analyses were performed using LSRII flow cytometer (BD Biosciences, San Jose, Calif.) and FlowJo software (Tree Star Inc, Ashland, Oreg.). The following anti-human antibodies were used for staining: CD25, CD45RO, CCR5, CCR6 (BD Biosciences), interferon (IFN)-γ (eBioscience), and IL-17 (Biolegend), IL-22 (R&D). For phospho-SMAD (Cell Signaling) staining, cells were fixed with BD cytofix buffer prewarmed to 37 C for 10 minutes, followed by permeabilization with ice-cold BD Phosphoflow Perm buffer III on ice for 30 minutes, and were then stained with the phospho-antibody for 1 hour at RT, followed by goat anti-Rabbit APC (Molecular Probes).

Transfections and Assay for Active TGFβ in the Supernatant

Statistical Analysis

All statistical analyses were performed with GraphPad Prism Software (GraphPad Inc., La Jolla, Calif.). The significance was determined using One-Sample Student's t-test. $P<0.05$ is considered significant.

Identification of a Metalloprotease Expressed on Memory CCR6+Cells

In order to identify novel molecules pertinent to the Th17 population among other human T cell subsets, human T cells were isolated as previously described. Microarray analysis of CCR6+ and CCR6−CD4+ T was performed as resting or after activation through the TCR (FIG. 1A), Metalloprotease ADAM12 was highly expressed on both CCR5+ and CCR5−CCR6+ T cells compared to CCR6 subset (FIG. 1B). Because ADAM12 was previously implicated in TGFβ signaling and in autoimmunity, this gene function vas characterized in Th17 cell differentiation or function.

To confirm the preferential expression of ADAM12 in memory CCR6+ quantitative real time PCR (qrt-PCR) of ADAM12 gene expression in all T cell subsets that were activated through the TCR was performed. Consistent with the microarray data, ADAM12 was expressed more than 100-500 fold in CCR6+compared to CCR6-cells (FIG. 1C). This expression pattern correlates with the expression level of Th17 signature genes (IL-17 and RORgt) both in the microarray and by qrt-PCR (data not shown and FIG. 1C). The expression of ADAM12 in CCR6+ cells from multiple donors was confirmed using IL-17 as a control (FIG. 1C, right). CCR6− cells did not express ADAM12 or IL-17 (FIG. 1C).

To determine the kinetics of ADAM12 expression in different Tcell subsets, qrt-PCR analysis for ADAM12 expression in naïve and memory CCR6+ cells either at a resting state or at different time points post TCR activation was performed. ADAM12 decreased day 1 after TCR stimulation in memory CCR6+ cells, and increased to resting stage levels after 3 days, and was absent in resting or activated Naïve cells (FIG. 1D and data not shown). The decrease in ADAM12 levels at day 1 correlated with a significant increase in IL-17 transcripts (FIG. 1D).

Figure 2B:
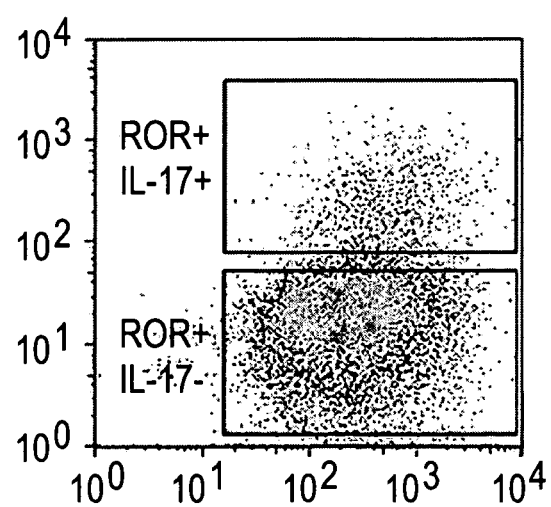
Figure 2D:
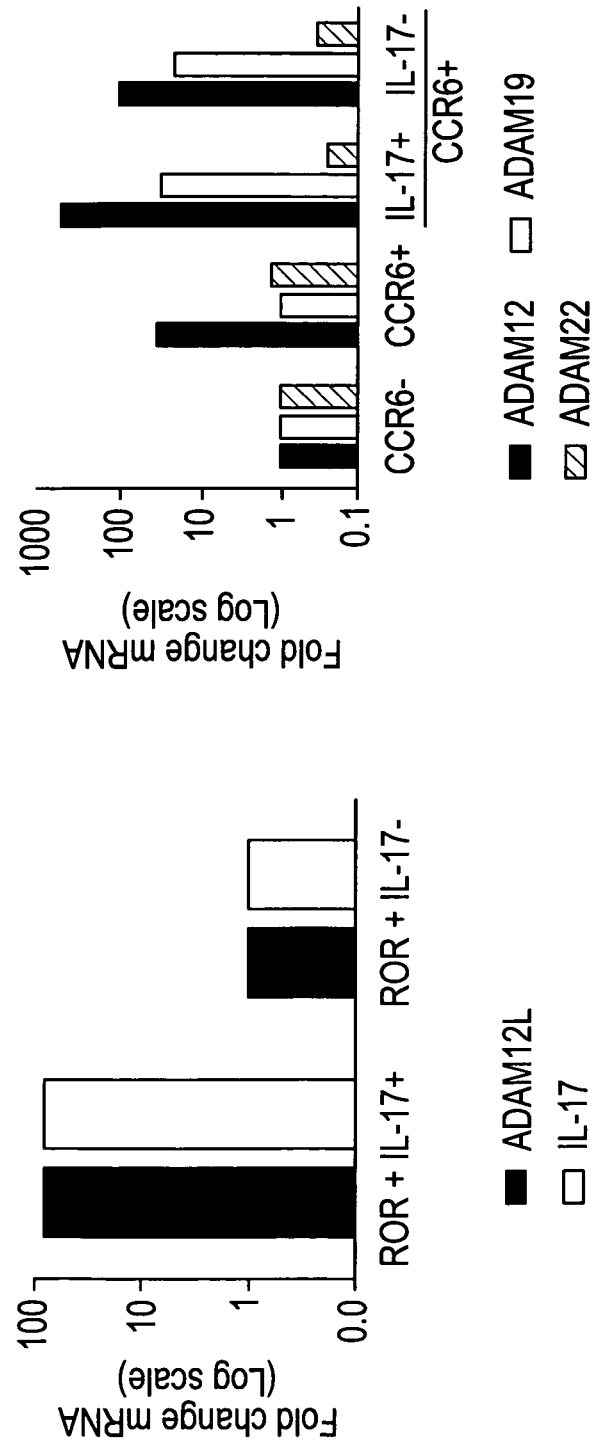

ADAM19 along with ADAM12, was expressed at significantly higher levels in T cells compared to myeloid cells sorted from the central nervous system of EAE mice. This T cell specific expression also prompted us to examine the expression of ADAM19 in human CCR6+ and purified Th17 cells. There was no difference by qrt-PCR of the expression of ADAM19 among all T cell subsets (FIG. 1E, 2D). ADAM22 was also detected in the microarray we performed in CCR6+ cells, so we wanted to test it along with ADAM19 as another marker of specificity for expression of ADAM12. The transcript level of ADAM22 was similar to that of ADAM19 (FIG. 1E, 2D). This emphasizes the specificity of ADAM12 expression in human memory CCR6+ and Th17 cells.

Expression of ADAM12 in ROR-Transduced and Ex-Vivo Isolated Th17 Cells

Because ADAM12 expression correlated with IL-17 and RORC expression (FIG. 1C), whether RORC can induce ADAM12 expression was investigated. For this experiment, T cells were activated and transduced with control (empty vector, EV) or RORgt-expressing lentiviruses that have GFP as a marker gene, and then expanded in IL-2-containing medium. The cells were sorted for GFP+ and then RNA was extracted for qrt-PCR. As shown in FIG. 2A, ROR-expressing cells had 10-fold higher ADAM12 and 20 fold higher IL-17 compared to controls.

In order to determine if ADAM12 expression was exclusively restricted to IL-17-secreting cells or all CCR6+ cells, a technique of ex-vivo isolation of Th17 cells from Streck et al. was adapted. Briefly, ROR overexpressing cells (FIG. 2B) were activated as described with several modifications as mentioned in methods section, and sorted based on expression of IL-17 into IL-17+ and IL-17−. Post sort, ADAM12 and IL-17 transcripts expression were analyzed in each of the sorted subsets and found that ROR+IL-17+contained 100 fold higher ADAM12 gene expression compared to ROR+IL-17− cells (FIG. 2B). The same technique of ex-vivo isolation of IL-17+ cells was used to isolate Th17 cells from fresh and purified CD4+ cells that were sorted into CD45RO+CCR6+ or CD45RO+CCR6− cells. CD45RO+CCR6+ cells were stained with IL-17 antibody and sorted into CCR6+IL-17+ and CCR6+IL-17−. Post sort, ADAM12 and IL-17 transcripts expression were analyzed in each of the sorted subsets and found that CCR6+IL-17+expressed 10 fold more ADAM12 compared to CCR6+IL-17− (FIG. 2C). Ex-vivo purified Th17 cells did not express ADAM19 or ADAM22 (FIG. 2D).

Figure 3A:
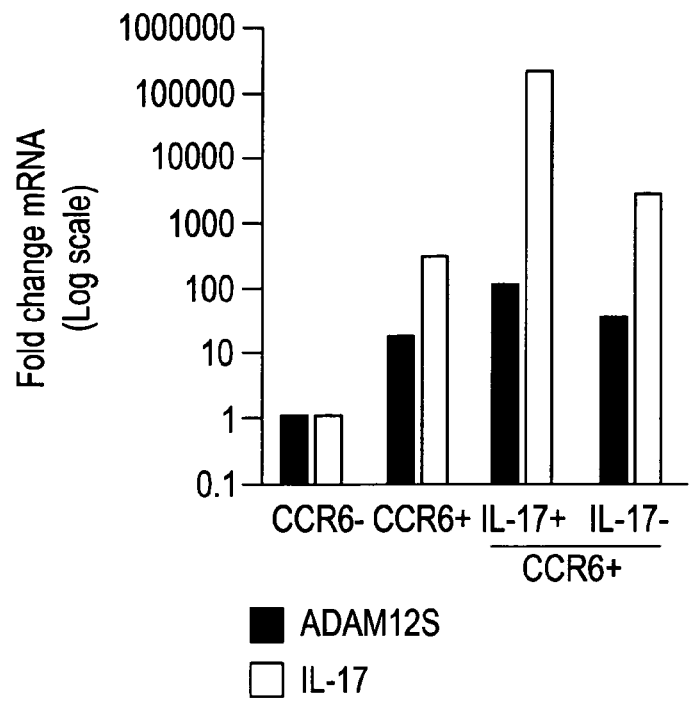
FIG. 3 demonstrates that a splice variant of ADAM12 is also expressed in Th17 cells, albeit at lower level. (A) Levels of ADAM12-S in T cell subsets, identified in FIG. 2C, using specific primers for ADAM12-S as determined by qrt-PCR. (B) Comparison of the mRNA levels of ADAM12-L and -S by qrt-PCR in CCR6+ and CCR6+IL-17+ T cells. One experiment representative of three donors is shown.
Figure 3B:
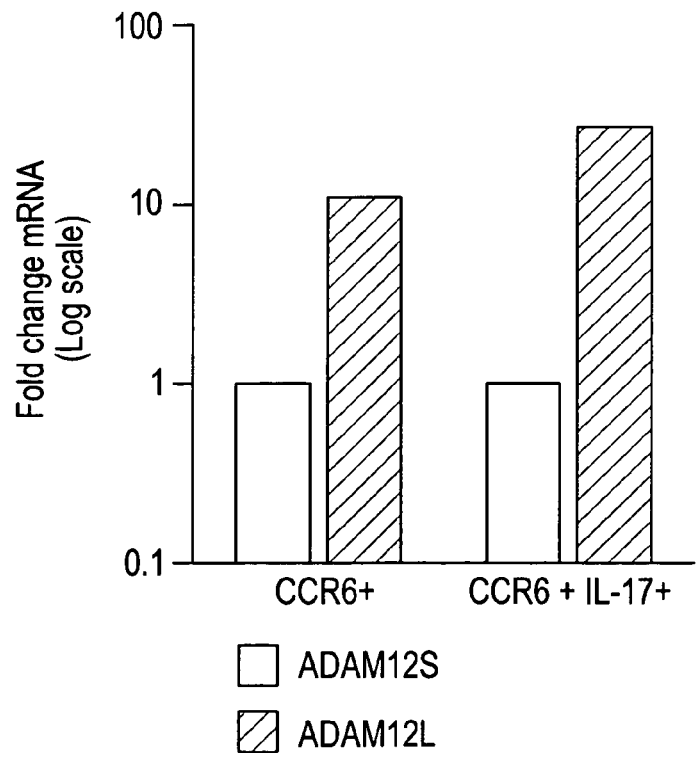

A Splice Variant of ADAM12 is also Expressed in Th17 Cells, Albeit at Lower Levels Two naturally occurring forms of human ADAM12 splice variants exist, called the long (ADAM12-L) and short (ADAM12-S) forms. The ADAM12-L protein composition suggests cell surface expression, while ADAM12-S appears to be the secreted form that lacks both the transmembrane and the cytoplasmic domains. Using primers specific for ADAM12-S transcript, by qrt-PCR, ADAM12-S, similar to ADAM12-L, was demonstrated to be specifically expressed in CCR6+ and ex-vivo purified Th17 cells (FIG. 3A). Albeit, ADAM12-S mRNA was about 10 fold lower in CCR6+ and 30 fold in CCR6+IL-17+as compared to ADAM12-L transcript (FIG. 3B).

Silencing ADAM12 in CCR6+ Cells Alters TGFβ Responsive Genes

Figure 4A:
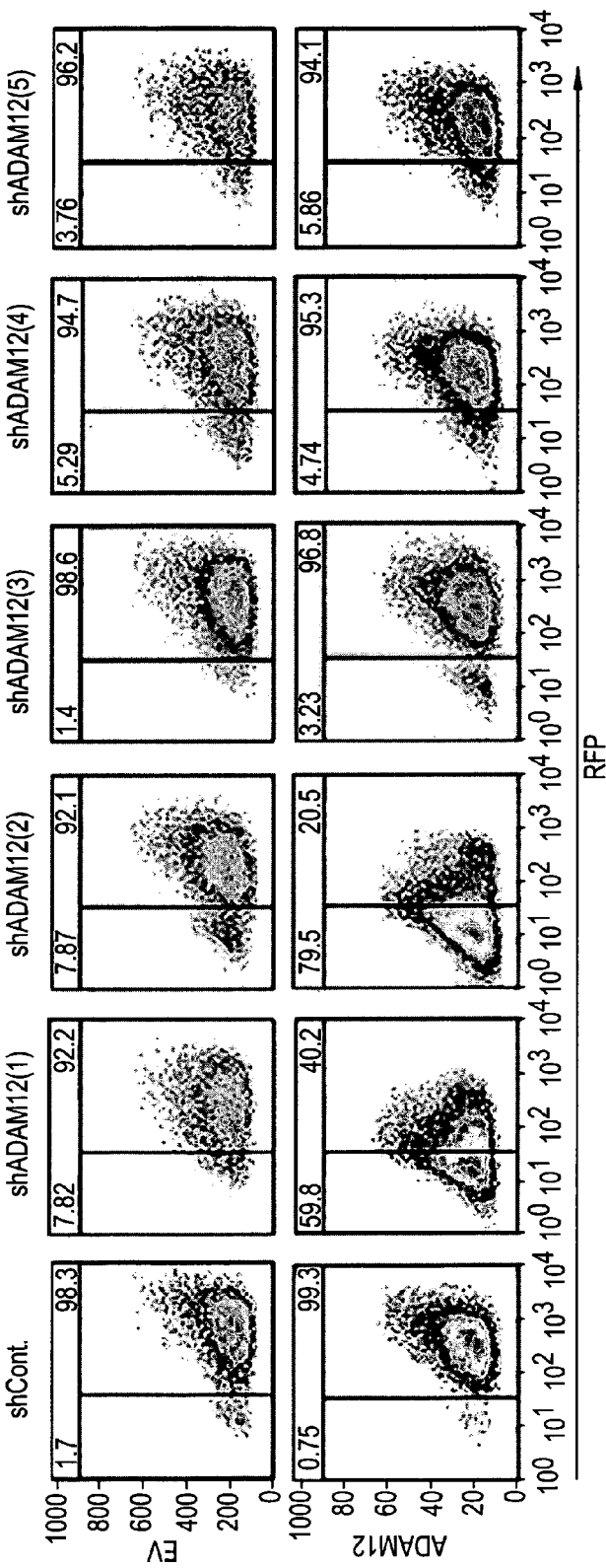
FIG. 4 demonstrates validation of ADAM12 silencing at both the protein and the mRNA levels. (A) 293T cells infected with ADAM12-expressing lentivirus or control vector that express RFP as a marker, were plated at 5 k cells and superinfected with 5 shRNAs targeting different regions of ADAM12 (shADAM12 1-5) or control shRNA (shCont.) that have a puromycin resistance gene. After 4 days, cells were transferred to 12 well plate and 3 days later cultured in puromycin containing media for 5-7 days. Non-infected 293T cells were used as a control for puromycin. Cells were collected at 2-3 day interval afterwards to assess for the expression of RFP. (B) mCCR6+ T cells were activated and transduced with 2 shRNAs to ADAM12 that showed a knock down of RFP expression in (A), followed by selection in puromycin before sorting for live cells. RNA was collected and the endogenous levels of ADAM12L and ADAM12S were determined by qrt-PCR.
Figure 4B:
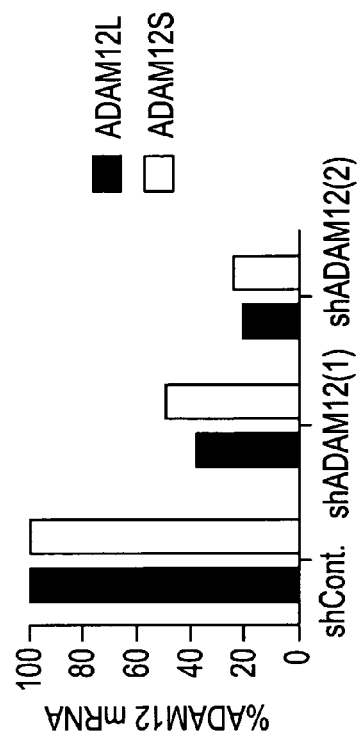

To examine the role of ADAM12 in CCR6+ cells, its expression was silenced using shRNAs. The shRNAs were selected based on their ability to reduce ADAM12 protein (FIG. 4A) and RNA levels (FIG. 4B) by at least 60%. Lentiviral transduction of CCR6+ T cells with ADAM12-shRNAs confirmed the reduced expression in primary T cells (FIG. 4B).

Figure 5C:
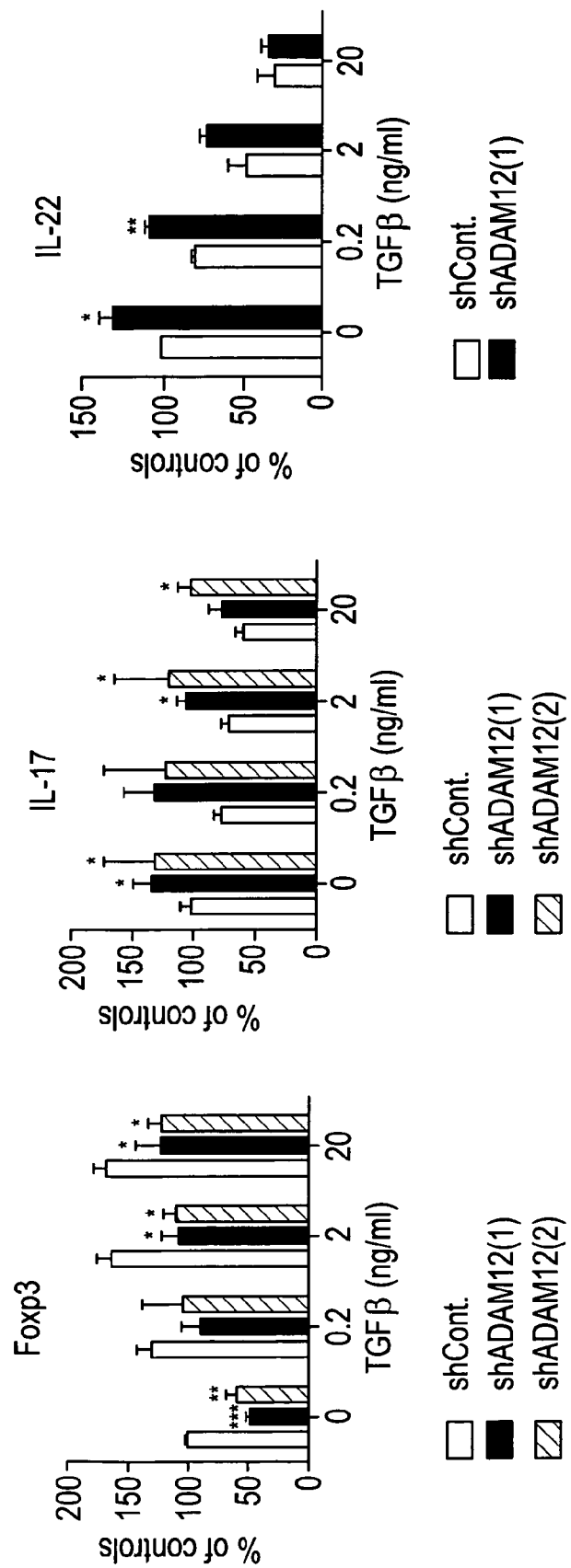
FIG. 5 demonstrates that silencing ADAM12 in CCR6+ cells alters TGFβ responsive genes. (A) Resting CD4+ CD45RO+CD25−CCR6+ T cells (TM CCR6+) were activated by TCR and simultaneously transduced with shADAM12 or its correspondent control (shCont.) that have puromycin resistance gene. The cells were cultured in IL-2 containing media for 4 days before the addition of puromycin (2 ug/ml) for 6 days. This was followed by ARIA sorting for live cells as depicted by the FACS plot, and restimulation of the sorted cells through TCR in the presence of TGFβ at the indicated concentrations for 3-6 days. On day 3, cells were collected for Foxp3 staining and on day 6, they were restimulated with P+I+ golgi stop and stained with antibodies against IL-17, and IL-22 as shown as FACS plot in (B) or as bar graph from multiple donors in (C). FACS plot from one representative donor was shown. Data are presented as mean percentage of cytokines+SEM from multiple donors and independent experiments. *<0.05, **<0.005

Silencing ADAM12 in CCR6+decreased Foxp3 levels by 50% and increased IL-17 production compared to control shRNA (FIG. 5B). Because Foxp3 is regulated by TGFβ signaling, how the addition of TGFβ in the absence of ADAM12 affects Foxp3 expression in these cells was investigated. Different concentrations of recombinant active TGFβ increased Foxp3 levels in cells expressing ADAM12 shRNA, however this increase was consistently lower than control cells (FIG. 5C). IL-17 and IL-22 expression were examined and found that TGFβ stimulation decreased IL-17 and IL-22 production in a dose dependent way in control CCR6+ T cells. In contrast to Foxp3, IL-17 and IL-22 levels increased in cells with reduced ADAM12 expression compared to control cells (FIG. 5C). Together, these data demonstrate that silencing ADAM12 in CCR6+ cells modulates their responsiveness to TGFβ signaling.

In order to dissect the relationship between TGFβ and ADAM12, whether ADAM12 was regulating signaling transduction downstream of TGFβ receptors was investigated. For this experiment two TGFβ-signaling inhibitors were used, which abolish the effect of TGFβ on TGFβ responsive genes as measured by Foxp3, IFNγ and IL-17 protein levels both in naïve and memory T cells (FIG. 6A, 6B).

Figure 7A:
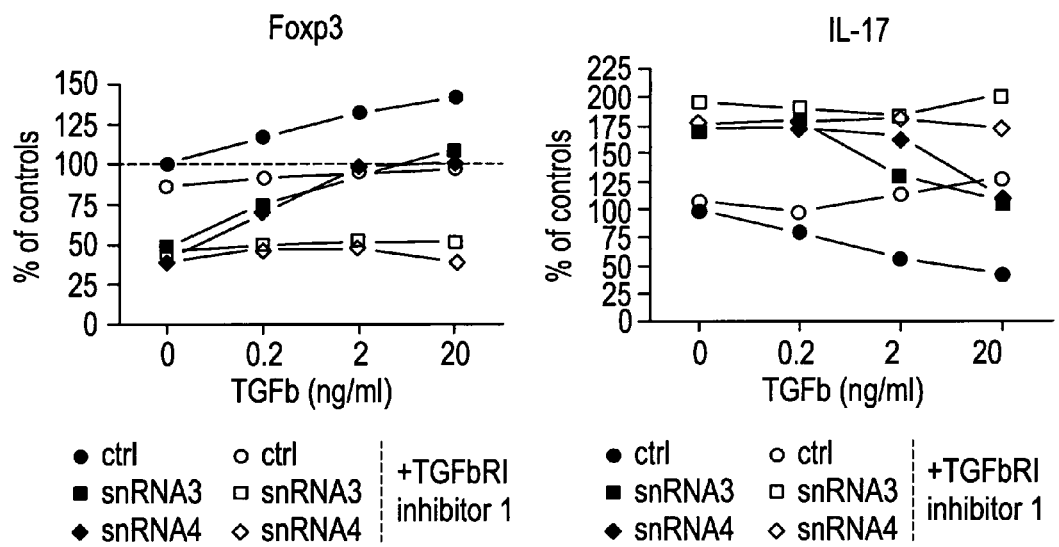
FIG. 7 shows that the use of TGFβR signaling inhibitors blocks TGFβ responses in ADAM12-silenced mCCR6+. The cells were activated and transduced as above (FIG. 5). Post sort for live cells, they were activated through the TCR and simultaneously pre-incubated with 1 uM of SJN2511-Tocris (inbibitor1) and 2.5 uM of SB-525334-Calbiochem (inhibitor2) for 60 min followed by the addition of TGFβ at the indicated concentrations. Cells were stained for Foxp3-Alexa647 on day 3 and for IL-17-percp-cy5.5 on day 6 after P+I stimulation. Two different inhibitors were used as depicted in (A) for inhibitor 1 and in (B) for inhibitor 2. One experiment representative of three donors is shown.
Figure 7B:
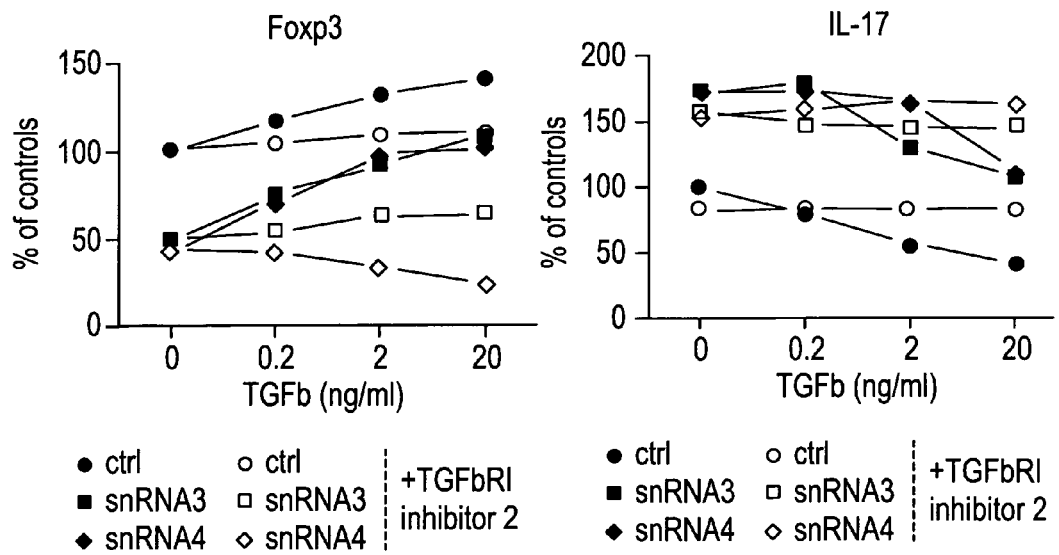

Control cells or cells silenced for ADAM12 were preincubated with TGFβ inhibitors before adding different amounts of TGFβ. The signaling was blocked as determined by abrogating the increase in Foxp3 and the decrease in IL-17 protein levels following TGFβ treatment. TGFβ-signaling in cells silenced for ADAM12 expression was completely suppressed by the inhibitors; similar to control cells (FIG. 7A, 7B). Interestingly, while t inhibitors did not alter the levels of Foxp3 and IL-17 in the absence of exogenous TGFβ, ADAM12-silenced cells showed 50% reduction in Foxp3 and 75% increase in IL-17 in this condition (FIG. 7A, 7B). This finding demonstrates that ADAM12 is not acting downstream of receptor signaling.

Ectopic Expression of ADAM12 in Naïve T Cells Mimics the Addition of Exogenous TGFβ

Figure 8A:
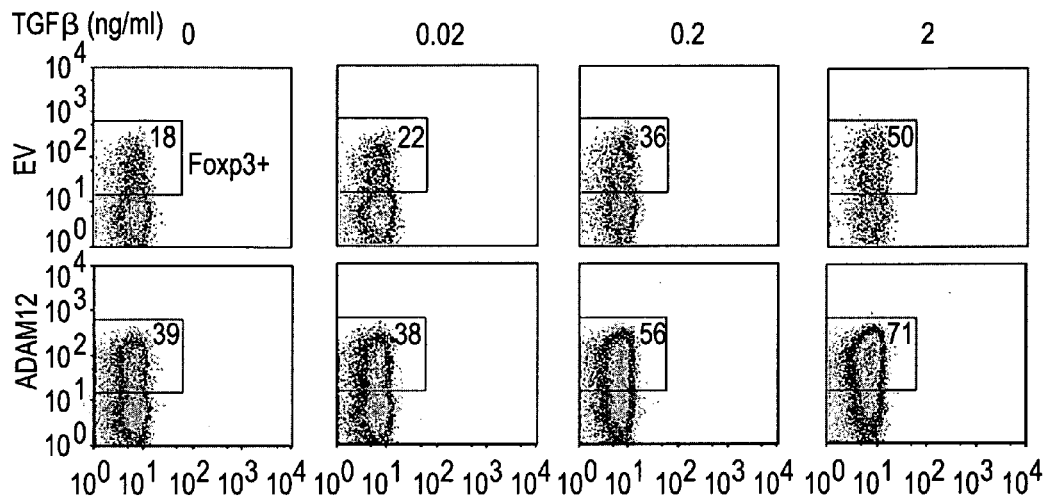
FIG. 8 demonstrates that ectopic expression of ADAM12 in naïve cells mimics the addition of exogenous TGFβ. Naïve T cells were TCR activated and simultaneously transduced with ADAM12 or vector control (EV) that have RFP as a marker gene for 4-6 days. The cells were then sorted based on RFP expression, restimulated in the presence of TGFβ at the indicated concentrations as in (A) or pretreated with TGFβ inhibitors (1 uM of Inhibitor1 and 2.5 uM of Inhibitor2) before the addition of TGFβ as shown in (B). Foxp3 was measured on day 3 in (A) and (B) using anti-Foxp3-Alexa647. Inh1, inhibitor 1 and Inh2, inhibitor2. One FACS plot is shown as representative of 3 donors.
Figure 8B:
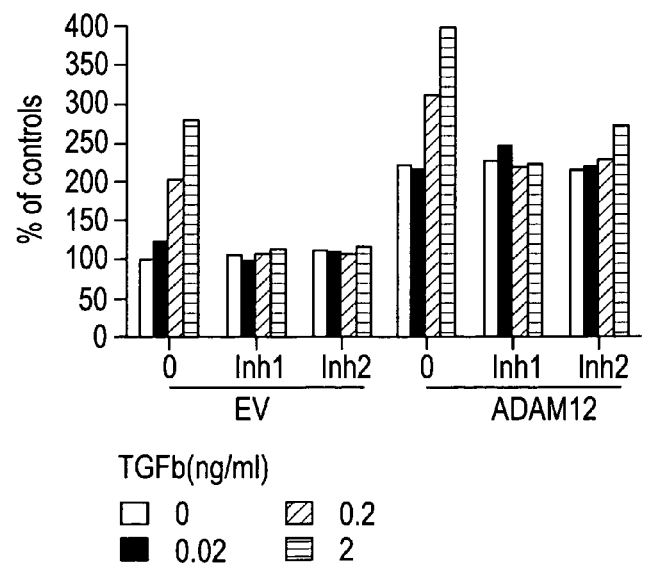

To further explore and confirm the role of ADAM12 in TGFβ pathway, human ADAM12 was subcloned into a HIV-derived vector (HDV) that encodes red fluorescent protein as a marker. Naïve T cells identified as CD25−CD45RO− were activated through the TCR with CD3 and CD28 coated beads, and transduced with HDV encoding ADAM12 or vector only (EV) as control. The cells were expanded in IL-2-containing media for few days, and were then sorted based on the expression of REP. They were then reactivated through the TCR and treated with different concentrations of TGFβ to induce endogenous Foxp3 in the presence or absence of two TGFβRI inhibitors. T cells that ectopically express ADAM12 had 2-fold higher Foxp3 levels and secreted less IFNγ compared to T cells transduced with control vector (FIG. 8A and data not shown). The addition of exogenous TGFβ further increased Foxp3 levels in ADAM12 overexpressing cells in a dose dependent manner similar to vector control cells (FIG. 8A). Pre-incubating the cells with TGFβ inhibitors completely blocked TGFβ signaling and impaired the cells from responding to exogenous TGFβ both in the control and ADAM12 expressing cells (FIG. 8B).

ADAM12 Functions Independent of Activating Latent TGFβ

Whether ADAM12 directly activated latent-TGFβ through its protease activity, which could explain its effect on amplifying TGFβ signals, was investigated. 293T cells were transfected with a plasmid encoding TGFb1 gene or control vector for 24-36 hours. The supernatant was then collected and tested for the amount of TGFβ produced using different serial dilutions on Jurkat overexpressing GARP molecule that directly binds latent TGFβ. To test for active TGFβ in the supernatant, epithelial lung Mink cells that express Luciferase under the control of TGFβ responsive-PAI promoter were used. These cells respond to active TGFβ and show high luciferase reading when cultured for overnight in TGFβ containing media or supernatant.

Figure 9A:
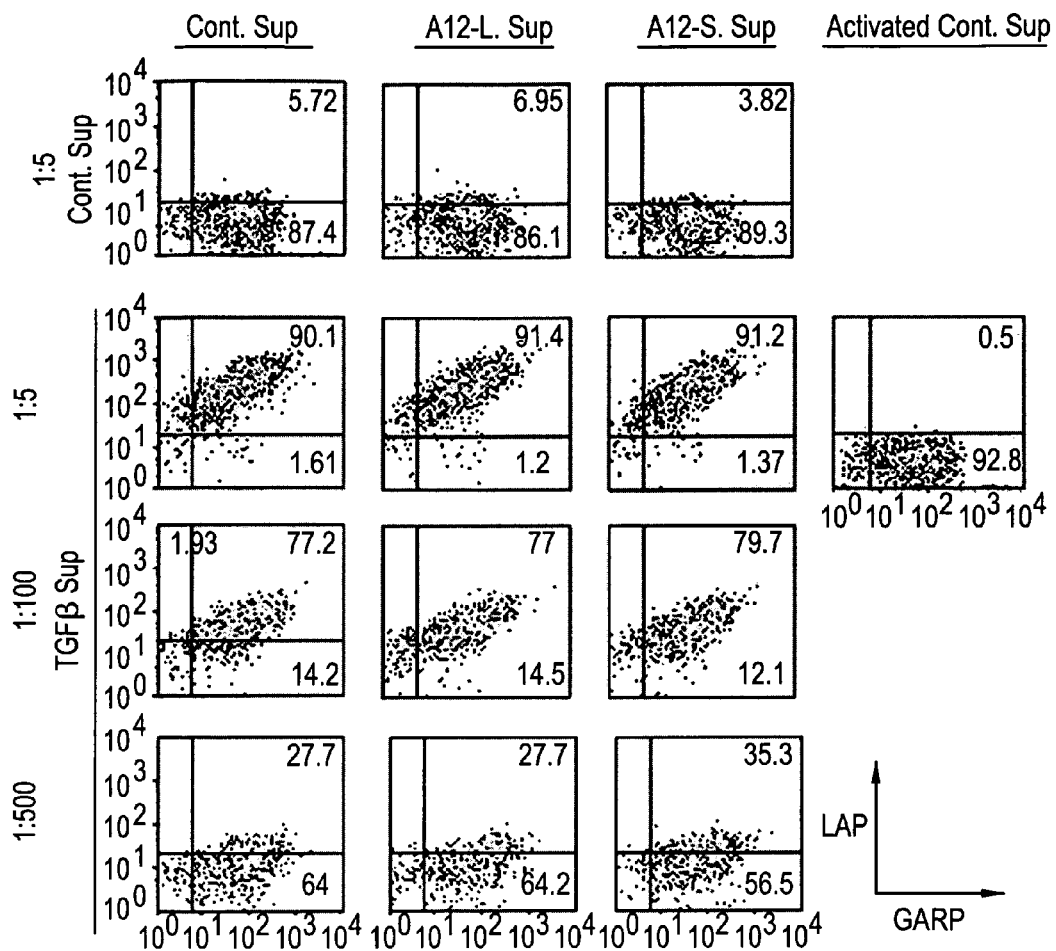
FIG. 9 indicates that ADAM12 functions independent of activating latent TGFβ. Supernatant collected from 293T cells transfected with ADAM12-cDNAs or control vector in the presence or absence of TGFβ supernatant were tested as described in the materials and methods for inactive TGFβ in Jurkat-GARP cells (A) or active TGFβ in MLC-PAI Luciferase cells (B).
Figure 9B:
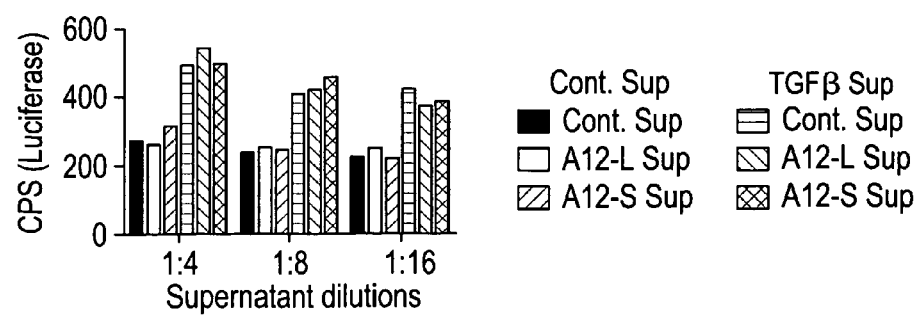

After validation of the supernatant, 293T cells were transfected with human ADAM12-L and -S fused to a myc tag as a marker gene or with CMV6 vector only as a control in the presence or absence of TGFb1 supernatants. ADAM12 expression was verified by flow cytometry using anti-myc antibody (data not shown). The supernatants from these transfected 293T cells was then collected from each condition and tested for inactive and active TGFβ as described above. GARP-overexpressing Jurkat cells showed similar LAP staining when incubated with the supernatant collected from cells that ectopically express ADAM12 compared to vector control alone (FIG. 9A). Also, when tested on Mink cells, the supernatant from ADAM12 expressing 293T did not display higher TGFβ activity compared to control supernatant (FIG. 9B). Collectively, this data demonstrate that ADAM12 does not activate latent TGFβ in the assay systems used herein.

ADAM12 is Expressed in Regulatory T Cells

Figure 10A:
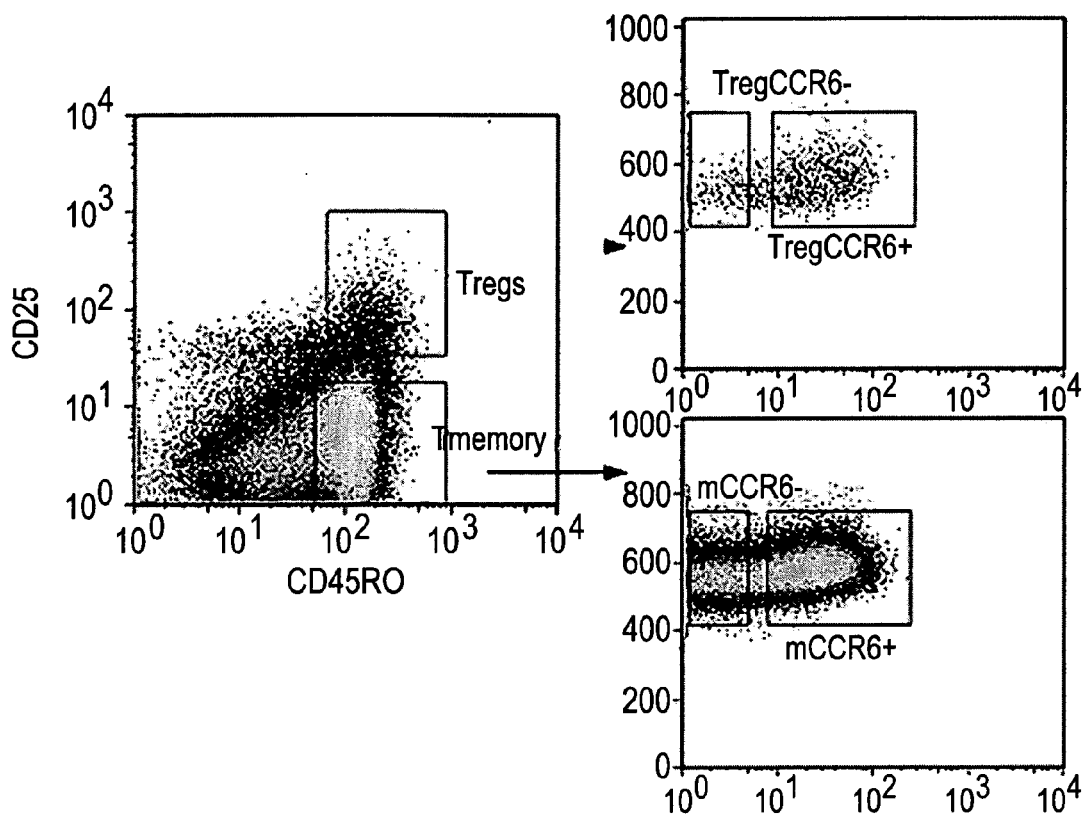
FIG. 10 depicts that ADAM12 is expressed in Treg cells. (A) CD4$^+$ T cells isolated from human PBMCs were stained with CD45RO-FITC and CD25-PE to isolate Tregs (CD45RO+CD25+) and memory (CD45RO+CD25−) Tcells. Each of the subsets was then further sorted based on CCR6 expression into TregCCR6− and TregCCR6+or mCCR6− and mCCR6+; m, memory T cells. (B) T-cell subsets identified in (A) were TCR activated for 24 hrs and ADAM12 mRNA levels along with IL-17 and Foxp3 were determined as shown in (B). One experiment representative of three donors is shown.
Figure 10B:
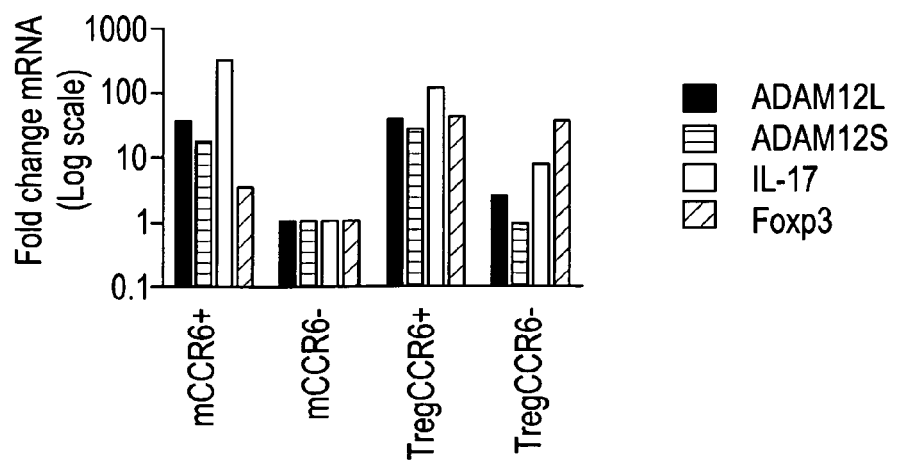

Because both Th17 and Tregs require TGFβ for their development and these data demonstrate that ADAM12 regulates TGFβ responses in Th17 cells. Tregs were isolated from the blood of adult healthy individuals as described. Tregs (CD25+CD45RO+) and memory T cells (CD25−CD45RO+) were further sorted based on CCR6 expression into 4 subsets: CCR6+CD25−, CCR6−CD25−, CCR6+CD25+, and CCR6−CD25+(FIG. 10A). Each of the cell subsets was stimulated overnight using a plate coated with anti-CD3, along with soluble CD28. Qrt-PCR was then performed on RNA isolated from each of the activated cells using primers for ADAM12, IL-17 and Foxp3. As shown in FIG. 10B, Tregs identified by high expression of Foxp3, also expressed ADAM12-L and S transcripts to a level comparable to mCCR6+.

We claim:

1. A method for decreasing signaling of a TGF in a T cell comprising decreasing the biological activity or expression of an ADAM by administering an agent that functions to inhibit the expression or biological activity of an ADAM wherein the agent is an interfering RNA or an antibody.

2. The method of claim 1 wherein the TGF is TGFβ.

3. The method of claim 1 wherein the ADAM is ADAM12.

4. A method for decreasing signaling of a TGF in a T cell according to claim 1 wherein the T cell is a helper T cell.

5. A method for decreasing signaling of a TGF in a T cell according to claim 1 wherein the T cell is a Th17 cell.

6. A method for decreasing signaling of a TGF in a T cell according to claim 1 wherein the T cell is an iTreg cell.

* * * * *

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: synthetic

```
<400> SEQUENCE: 1
gcccgcgggc attgccatgg cagcgcgccc gctg                              34

<210> SEQ ID NO 2
<211> LENGTH: 34
<212> TYPE: DNA
<213> ORGANISM: Artificial Sequence
<220> FEATURE:
<223> OTHER INFORMATION: synthetic

<400> SEQUENCE: 2
gaccgcggcc ggccgtttaa accttatcgt cgtc                              34
```